United States Patent [19]

Goldstein et al.

[11] Patent Number: 4,505,853

[45] Date of Patent: Mar. 19, 1985

[54] ENZYME-RESISTANT IMMUNOMODULATORY PEPTIDES

[75] Inventors: Gideon Goldstein, Short Hills; George Heavner, Flemington; Daniel Kroon; Tapan Audhya, both of Bridgewater, all of N.J.

[73] Assignee: Ortho Pharmaceutical Corporation, Raritan, N.J.

[21] Appl. No.: 553,281

[22] Filed: Nov. 18, 1983

[51] Int. Cl.³ .................... C07C 103/52; A61K 37/00
[52] U.S. Cl. .......................................... 260/112.5 R
[58] Field of Search .................. 260/112.5 R; 424/177

[56] References Cited

U.S. PATENT DOCUMENTS

| 4,190,646 | 2/1980 | Goldstein et al. | 260/112.5 R |
| 4,261,886 | 4/1981 | Goldstein et al. | 260/112.5 R |
| 4,298,523 | 11/1981 | Heavner | 260/112.5 R |
| 4,369,137 | 1/1983 | Heavner | 260/112.5 R |

*Primary Examiner*—Delbert R. Phillips
*Attorney, Agent, or Firm*—Geoffrey G. Dellenbaugh

[57] ABSTRACT

Peptides which have thymopoeitin-like or splenin-like activity combined with greatly increased resistance to degradation by enzymes. The peptides are useful for treatment of immunoregulatory disorders. Also provided are methods of treating immunoregulatory disorders and compositions used in these methods.

28 Claims, No Drawings

ENZYME-RESISTANT IMMUNOMODULATORY PEPTIDES

BACKGROUND OF THE INVENTION

1. Field of the Invention

This invention relates generally to new immunomodulatory peptides and particularly to such peptides which have improved resistance to enzymatic degradation in the body.

2. Description of the Prior Art

U.S. Pat. Nos. 4,190,646 and 4,261,886 disclose various pentapeptides having activity similar to the long chain polypeptide known as thymopoietin described in U.S. Pat. Nos. 4,002,740 and 4,077,949. The above patents are all incorporated herein by reference. The biological activity of certain of these peptides is described in an article by M. E. Weksler, et al., J. Exp. Med. 148:996–1006 (1978). This article is also incorporated herein by reference. Published European Patent Application No. 25,897 and U.S. Pat. No. 4,361,673 also disclose various peptides asserted to have activity similar to thymopoietin. Thymopoietin III, also known as "splenin", is a similar peptide isolated from bovine spleen. Audhya, et al., Biochemistry, 20, 6195–6200 (1981). This material stimulates induction of both T cells and B cells.

Reference is made to the above-described patents, patent application, and articles for a discussion of other background material and the biological processes involved in the present invention.

Although these known peptides are useful for their immunomodulatory activity, they have been found to be rapidly destroyed by enzymes both in vitro and in vivo after administration to an animal or human recipient. See, for example, Int. J. Pept. and Protein Res., 14, 479–484 (1979); ibid, 22:187–193 (1983).

The present invention provides peptides and peptide compositions which are more resistant than the prior art peptides to enzymatic degradation in the body and hence are more therapeutically useful materials.

SUMMARY OF THE INVENTION

The present invention relates to novel peptides having the following formula:

$$R-V-W-X-Y-Z-R^1 \quad (I)$$

or a pharmaceutically-acceptable acid- or base-addition salt thereof;
wherein
R is H, NH$_2$, acyl-NH, CH$_3$NH or pyro-GLU-NH;

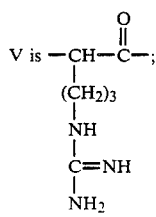
V is

W is PRO, dehydro PRO, or

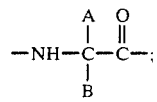

A individually is loweralkyl;
B individually is H if A is C$_4$–C$_6$ loweralkyl and is otherwise C$_1$–C$_3$ loweralkyl;
A and B taken together are —(CH$_2$)$_4$— or —(CH$_2$)$_5$—;
X is D-ASP, ASP, D-GLU, or GLU;
Y is GLY, VAL, LEU, nor-LEU, PHE, ILE, LYS, GLN, GLU, ALA, D-VAL, D-LEU, D- nor LEU, D-PHE, D-ILE, D-LYS, D-GLN, D-GLU, or D-ALA;
Z is

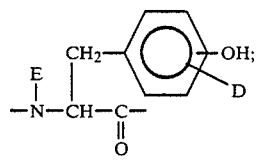

D is H or 1 or 2 substituents which increase or do not substantially decrease the acidity of the phenol proton;
E is H or C$_1$–C$_3$ loweralkyl;
R' is OH, NHR",

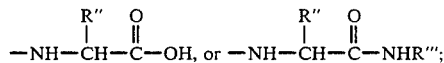

and
R" and R'" are individually H or lower alkyl;
provided that no more than one of V, X, and Y is a D amino acid.

Whenever R is other than H, V may occur in D or L form. Both D and L forms of Z are also included within the present invention. If A and B are different, optical isomers are possible for this value of W; both the D- and L-isomer are included in the present invention, although the L-isomer is preferred.

Also provided by the present invention are therapeutic compositions containing the subject peptides and methods for treatment of humans and animals by administration of these peptides and the compositions.

It has been surprisingly found that the subject peptides possess thymopoietin-like or splenin-like activity and, because of the presence of the W group at position 2, are resistant to attack by endo- and exopeptidases and trypsin-like enzymes in serum.

DETAILED DESCRIPTION OF THE INVENTION

As indicated above, this invention is concerned with new peptides having thymopoietin-like or splenin-like activity, therapeutic compositions containing these peptides, and methods for use thereof.

In its broadest scope, the present invention provides peptides having the following formula:

$$R-V-W-X-Y-Z-R^1 \quad (I)$$

or a pharmaceutically-acceptable acid- or base-addition salt thereof wherein R, V, W, X, Y, Z, and R' are as defined above.

Preferred peptides of the present invention are those of formula I wherein R is acyl-NH and W is PRO or AIB. More preferred peptides are those of formula I wherein R—V is acyl-ARG, W is PRO or AIB, X is ASP or GLU, Y is GLY or an L amino acid as previously defined, Z is TYR or D-substituted TYR, and $R^1$ is OH or $NH_2$. Still more preferred peptides are those of formula I wherein R—V is acetyl-ARG, W is PRO or AIB, X is ASP or GLU, Y is GLY or an L amino acid as previously defined, Z is TYR or D-substituted TYR, and $R^1$ is $NH_2$. The most preferred peptide is N-acetyl-ARG-PRO-ASP-VAL-TYR-$NH_2$.

As used herein the term "lower alkyl" includes branched and straight-chain saturated hydrocarbons having from one to six carbon atoms, such as methyl, ethyl, propyl, isopropyl, pentyl, hexyl, and the like. The term "acyl" includes formyl and loweralkyl carbonyl radicals such as acetyl, propionyl, succinoyl, and the like.

Representative D substituents which increase the acidity of the phenol porton of the Z amino acid residue are, for example, 3-chloro and 3-nitro. Those skilled in the peptide art would recognize that other electron withdrawing groups, especially at the 3-position of the phenyl ring of Z, would increase the acidity of the phenol proton, as would groups which stablize the phenoxide ion resulting from donation of the phenol proton.

As acids which are able to form salts with these peptides there may be mentioned inorganic acids such as hydrochloric acid, hydrobromic acid, perchloric acid, nitric acid, thiocyanic acid, sulfuric acid, phosphoric acid, and the like, and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, napthalene-sulfonic acid, sulfanilic acid, or the like.

As bases which are able to form salts with these peptides are included inorganic bases such as sodium hydroxide, ammonium hydroxide, potassium hydroxide, and the like and organic bases such as mono-, di- and tri-alkyl and aryl amines (e.g., triethylamine, diisopropylamine, methylamine, dimethylamine, and the like) and optionally substituted ethanolamines (e.g., ethanolamine, diethanolamine, and the like).

Throughout this disclosure, the amino acid components of the peptides and certain materials used in their preparation are identified by abbreviations for convenience. These abbreviations are as follows:

| Amino Acid | Abbreviated Designation |
| --- | --- |
| α-methylalanine | AIB |
| cycloleucine | CLE |
| 4-methyl leucine | 4-methyl-LEU |
| glycine | GLY |
| L-alanine | ALA |
| D-alanine | D-ALA |
| L-arginine | ARG |
| D-arginine | D-ARG |
| L-aspartic acid | ASP |
| D-aspartic acid | D-ASP |
| L-dehydroproline | dehydroPRO |
| L-glutamic acid | GLU |
| D-glutamic acid | D-GLU |
| L-glutamine | GLN |

| Amino Acid | Abbreviated Designation |
| --- | --- |
| D-glutamine | D-GLN |
| L-isoleucine | ILE |
| D-isoleucine | D-ILE |
| L-leucine | LEU |
| D-leucine | D-LEU |
| L-lysine | LYS |
| D-lysine | D-LYS |
| L-norleucine | nor-LEU |
| D-norleucine | D-nor-LEU |
| L-proline | PRO |
| L-tyrosine | TYR |
| L-valine | VAL |
| D-valine | D-VAL |

The term "dehydroPRO" includes 2,3-dehydroPRO, 3,4-dehydroPRO, and 4,5-dehydroPRO; 3,4-dehydroPRO is preferred.

The peptides of the invention may generally be prepared following known techniques. Conveniently, the peptides may be prepared following the solid-phase synthetic technique initially described by Merrifield in Journal of the American Chemical Society, 85, 2149–2154 (1963). Such methods are also disclosed in certain of the prior art patents referred to above. Other techniques may be found, for example, in M. Bodansky, et al., Peptide Synthesis, John Wiley & Sons, second edition, 1976. Appropriate protective groups usable in such syntheses and their abbreviations will be found in this text, as well as in "Protective Groups in Organic Chemistry", J. F. W. McOmie, Editor, Plenum Press, New York, 1973, both of which books are incorporated herein by reference. The common protective groups used herein are t-butyloxycarbonyl(BOC), benzyl(BZL), t-amyloxycarbonyl(AOC), tosyl(TOS), o-bromophenylmethoxycarbonyl(BrZ), and 26-dichlorobenzyl($BzlCl_2$).

The peptides of this invention wherein X is ASP or D-ASP have been found to exhibit biological activity similar to thymopoietin, as disclosed in the above-referenced U.S. patents and articles, while those wherein X is GLU or D-GLU have been found to exhibit biological activity similar to splenin. The compounds of the invention were tested following the induction assay procedure set out in Scheid, et al., J. Exp. Med. 147: 1727–1743 (1978) and also following a receptor assay procedure designed to measure displacement of radiolabelled thymopoeitin from a receptor site by the test peptides. A positive result on the induction assay indicates the ability of the test peptide to mimic the ability of thymopoietin or splenin to induce precursor cells to immunocompetent T cells or T cells and B cells, respectively. A positive result on the receptor assay indicates the ability of the test peptide to bind to the thymopoeitin receptor site and thus to mimic thymopoeitin activity. The subject peptides are positive in the induction assay, while those in which X is ASP or D-ASP are also positive in the receptor assay.

The peptides of the invention wherein X is ASP or D-ASP are characterized by their ability to induce the selective differentiation of Thy-1+ T cells (but not Lyb-2+ B cells). Thy-1 is a differentiation alloantigen present on T cells but not B cells, whereas Lyb-2 is a differentiation alloantigen present on B cells but not T cells. Studies of these peptides in the induction assay in vitro show them to have the same induction specificity as thymopoietin. That is, they induced the differentiation of Thy-1− cells to Thy-1+ T cells, but did not induce the differentiation of Lyb-2⁻ cells to Lyb-2⁺ B cells. The peptides of the invention wherein X is GLU or D-GLU are characterized by their ability to induce the differentiation of Thy-1⁻ cells to Thy-1⁺ T cells and also Lyb-2⁻ cells to Lyb-2⁺ B cells.

As noted above, it has been found that the prior art peptide fragments of thymopoeitin and splenin and their analogs suffer from very rapid enzymatic breakdown in the animal or human to whom they are administered. It has been determined that the half-life of thymopentin (thymopoeitin fragment 32-36) in serum is approximately one minute. Splenopentin (the corresponding fragment of splenin) is also highly susceptible to enzymatic degradation. The subject peptides, however, exhibit a substantially increased resistance to enzymatic degradation, up to 1000-fold better than thymopentin. This substantially increased stability of the subject peptides is evidenced against isolated enzymes of animal origin (e.g., leucine aminopeptidase of both cytosol and microsomal origin and carboxypeptidase A, B, and C) and against human serum. Illustrative stability data are shown in the following Tables.

TABLE 1

Stability of Peptides Against Leucine Aminopeptidase

| Peptide | Incubation time required for 50% degradation* (minute) |
|---|---|
| NH₂—Arg—Lys—Asp—Val—Tyr—OH (thymopentin) | 15 |
| NH₂—Arg—Pro—Asp—Val—Tyr—OH | 230 |
| N—Acetyl-Arg—Pro—Asp—Val—Tyr—NH₂ | >1400 |
| NH₂—Arg—Aib—Asp—Val—Tyr—OH | 1400 |
| NH₂—Arg—Cle—Asp—Val—Tyr—OH | >1400 |

*1 × 10⁻³ M peptide and 3 units/ml porcine LAP-cytosol in 50 mM Tris pH 8.5 buffer with 5 mM MgCl₂ at 37°

TABLE 2

Stability of Peptides Against Carboxypeptidase A

| Peptide | Incubation time required for 50% degradation* (minute) |
|---|---|
| NH₂—Arg—Lys—Asp—Val—Tyr—OH | 18 |
| NH₂—Arg—Aib—Asp—Val—Tyr—OH | 26 |
| NH₂—Arg—Aib—Asp—Val—Tyr—NH₂ | >450 |
| NH₂—Arg—Pro—Asp—Val—Tyr—NH₂ | >450 |
| N—Acetyl-Arg—Pro—Asp—Val—Tyr—NH₂ | >1500 |

*1 × 10⁻³ M peptide and 0.05 units/ml bovine carboxypeptidase A in pH 8.5 borate buffer at 37°

TABLE 3

Stability of Peptides Against Human Serum

| Peptide | Incubation Time Required for 50% degradation* (minute) |
|---|---|
| NH₂—Arg—Lys—Asp—Val—Tyr—OH | 1.5 |
| NH₂—Arg—Aib—Asp—Val—Tyr—OH | 32 |
| N—Acetyl-Arg—Aib—Asp—Val—Tyr—OH | 40 |
| NH₂—Arg—Aib—Asp—Val—Tyr—NH₂ | no degradation at 30 minutes |
| N—Acetyl-Arg—Pro—Asp—Val—Tyr—OH | 38 |
| NH₂—Arg—Pro—Asp—Val—Tyr—NH₂ | >20 |
| N—Acetyl-Arg—Pro—Asp—Val—Tyr—NH₂ | no degradation at 30 minutes |

*1 μg/ml peptide in fresh human serum at 37°

Prior to the making of the present invention, it was completely unexpected that one would be able to prepare peptides which would have equivalent or increased thymopoeitin-like or splenin-like activity while also having substantially increased resistance to enzymatic degradation. In fact, the present Applicants have found that many substitutions in the 2-position destroy or significantly diminish activity, while many other substitutions on the 2-positions retain activity but fail to confer enzyme resistance. Only the 2-position substitutions described herein provide peptides which simultaneously possess equivalent or enhanced biological activity and substantially increased resistance to enzymatic degradation, when compared to (for example) thymopoeitin.

Because of these characteristics of the subject peptides, they are therapeutically useful in the treatment of humans and animals since they have the capability for inducing the differentiation of lymphopoietic stem cell originating in the haemopoietic tissues into thymus-derived cells (T cells) which are capable of involvement in the immune response of the body. As a result, the subject peptides are considered to have multiple therapeutic uses. Primarily, since the compounds have the capability of carrying out certain of the indicated functions of the thymus, they have application in various thymic function and immunity areas. One such application is in the treatment of DiGeorge Syndrome, a condition in which there is a congenital absence of thymus. Injection of one of the subject peptides will overcome this deficiency. Because of the resistance of the subject peptides to enzymatic degradation, they are more therapeutically effective than prior art peptides having thymopoietin-like activity.

Additionally, the subject peptides are considered useful in assisting the collective immunity of the body, in that they will increase or assist in therapeutic stimulation of cellular immunity and thereby are useful in the treatment of diseases involving chronic infection, such as fungal or mycoplasma infections, tuberculosis, leprosy, acute and chronic and viral infections and the like.

The subject compounds are generally considered to be useful in any area in which cellular immunity is an issue and particularly where there are deficiencies in immunity such as in the DiGeorge syndrome mentioned above. Thus, where there is an excess of antibody production due to unbalanced T cells and B cells, the subject peptides can correct this condition by stimulating T cell production. Thus, they are expected to be of therapeutic use in certain autoimmune diseases in which damaging antibodies are produced, such as systemic lupus erythematosis, rheumatoid arthritis, or the like.

In their broadest application, the subject compounds are useful for regulating the immune system of a subject, human or animal, in need of such regulation. As used herein, the term "regulate" means that the subject compounds cause the immune system to return from an abnormal, diseased state to a normal, balanced state. While this regulation may well find great application in the correction of immunological deficiencies (e.g., DiGeorge syndrome), it is also applicable to correct conditions of excess immunological activity (e.g., autoimmune diseases). The present invention therefore includes methods for regulating the immune system of a subject in need of such regulation which comprises administering to said subject an immunoregulatorily-effective amount of one of the subject compounds, as well as pharmaceutical compositions for practicing these methods.

The present invention provides a method for treatment of conditions resulting from relative or absolute T cell deficiencies in a subject (human or animal) having such a condition which comprises administering to the subject a therapeutically-effective amount of a peptide of formula (I). The invention also provides a method for treatment of conditions resulting from relative or absolute deficiencies of the thymus of a subject which comprises administering to said subject a therapeutically-effective amount of a peptide of formula (I). As used herein, the term "therapeutically-effective amount" means an amount which is effective to treat conditions resulting from T cell deficiencies or deficiencies of the thymus, respectively. The invention also provides a method for inducing lymphopoietic stem cells of a subject to develop the characteristics of thymus-derived lymphocytes which comprises administering to the subject an effective inducing amount of a peptide of formula (I). The invention further provided pharmaceutical compositions for practicing those methods.

To prepare the pharmaceutical compositions of the present invention, a peptide of formula I or a base or acid addition salt thereof is combined as the active ingredient in intimate admixture with a pharmaceutical carrier according to conventional pharmaceutical compounding techniques. This carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, oils, alcohols, flavoring agents, preservatives, coloring agents and the like in the case or oral liquid preparation (e.g., suspensions, elixirs, and solutions) or carriers such as starches, sugars, diluents, granulating agents, lubricants, binders, disintegrating agents, and the like in the case of oral solid preparations (e.g., powders, capsules, and tablets). Controlled release forms may also be used. Because of their ease in administration, tablets and capsules represent the most advantageous oral dosage unit form, in which case solid pharmaceutical carriers are obviously employed. If desired, tablets may be sugar coated or enteric coated by standard techniques.

For parenteral products, the carrier will usually comprise sterile water, although other ingredients to aid solubility or for preservation purposes (for example) may be included. Injectable suspensions may also be prepared, in which case appropriate liquid carriers, suspending agents, and the like may be employed. The subject peptides are generally active when administered in amounts above about 10 μg/kg of body weight. For treatment of DiGeorge Syndrome, the peptides may be administered at a rate of about 10 to about 100 μg/kg body weight. Generally, the same range of dosage amounts may be used in treatment of the other diseases or conditions mentioned.

The following examples are presented to illustrate the invention without intending specifically limiting the invention thereto. In the examples and throughout the specification, parts are by weight unless otherwise indicated.

EXAMPLE I

$N^\alpha$-acetyl-Arginyl-Prolyl-Aspartyl-Valyl-Tyrosine amide

The peptide was synthesized by the solid phase method. The synthesis was begun with 4.16 g p-methylbenzhydrylamine resin, substitution level 0.39 mmol per gram, and the following amino acid derivatives were coupled stepwise with dicyclohexylcarbodiimide-hydroxybenzotriazole: BOC(BrZ)Tyr, BOC-Val, BOC-($\beta$-Bzl)Asp, BOC-Pro, and AOC-($N^g$-tosyl)Arg. The tyrosine was recoupled. The amyloxycarbonyl group was removed with trifluoroacetic acid, the resin was neutralized with diisopropylethylamine, and the amine acetylated with 15 percent acetic anhydride in dimethylformamide. After washing and drying, the resin weighed 6.08 g.

The peptide was cleaved from the resin with 60 ml liquid HF containing 6 ml m-cresol at 0° for 75 minutes. The HF was removed under reduced pressure. The residue was washed with ethyl acetate and ether, then the peptide extracted from the resin with 100 ml 5 percent acetic acid. The lyophilized extract weighed 1.042 g.

A 475 mg portion of the crude peptide was purified by chromatography on a 2.6×100 cm column of SP-Sephadex eluted with 0.05M ammonium acetate pH 5 at 50 ml per hour. Fractions 98–122 (10 ml each) were combined and lyophilized to yield 462 mg product, greater than 99 percent pure.

HPLC: rt=9.1 min with 12 percent $CH_3CN$—0.01M $NH_4OAc$ pH 5 at 1.5 ml/min on Whatman Porasil $C_{18}$.
TLC, silica gel 60:
$R_f$ 0.26 3:1:1 n-BuOH:HOAc:$H_2O$
$R_f$ 0.43 15:3:12:10 n-BuOH:HOAc:$H_2O$:pyr
$R_f$ 0.64 1:1 TFE:$NH_4OH$
Amino acid analysis: Asp, 0.99; Pro, 1.00; Val, 1.00; Tyr, 0.99; Arg, 1.01; 70 percent peptide.

EXAMPLE II

$N^\alpha$-Acetyl-Arginyl-Prolyl-Aspartyl-Glutamyl-Tyrosine

The peptide was prepared by the solid phase method, starting with BOC-Tyr(OBzlCl$_2$) resin ester (2536-138, 0.32 meg/g, 3.2 g). The following standard routines were used:

Deprotection—15 ml 50 percent TFA/$CH_2Cl_2$ for 1 min, then 15 ml 50 percent TFA/$CH_2Cl_2$ for 30 min;
Washing—15 ml $CH_2Cl_2$ twice for 1 min each, followed by 15 ml iPrOH for 1 min, then 15 ml $CH_2Cl_2$ twice for 1 min each;
Neutralization—15 ml 5 percent DIEA/$CH_2Cl_2$ twice for 2.5 min each;
Coupling—3.0 mmol of the protected amino acid (0.46 g) and HOBT were dissolved in 2 ml DMF and then diluted with 13 ml $CH_2Cl_2$. DCC (0.62 g) was dissolved in 3 ml $CH_2Cl_2$. Reaction time was 2 h.

One coupling each was required for $BOC^\alpha$-$Bzl^\gamma$-Glu, $BOC^\alpha$-$Bzl^\beta$-Asp, BOC-Pro, and $AOC^\alpha$-$Tos^g$-Arg. After a final deprotection, the resin peptide was acetylated for 60 min using 10 percent (v/v) $Ac_2O$ in 15 ml DMF and DMAP (300 mg).

The resin was cleaved in HF/anisole (30 ml/6 ml) for 60 min at 0° C. The cleaved resin residue was quenched with $Et_2O$, filtered and the solids extracted with 100 ml 8 percent HOAc for 30 min. After filtering, the filtrate was lyophilized to give 3219-69HF, 1.23 g.

The crude peptide was purified on Sephadex DEAE (2.6×90 cm column, 3 L 0.2M pH 7.8 $NH_4HCO_3$ followed by 2 L 0.33M pH 7.8 $NH_4HCO_3$, as elutent, 75 ml/n flow rate, 13 ml/fractions, 277 nm detection). Fractions 214–236 were collected and lyophilized to give the desired compound as a colorless solid, 450 mg, 53 percent.

| Amino Acid Analysis: | | |
|---|---|---|
| Amino Acid | Ratio | |
| Arg | 1.00 | |
| Pro | 1.04 | |
| Asp | 0.99 | 85.1 percent peptide content |
| Glu | 1.00 | |
| Tyr | 0.98 | |

| Thin Layer Chromatography: Silica Gel G, 250μ | | |
|---|---|---|
| Elutent | | $R_f$ |
| 3:1:1 | nBuOH:HOAc:H₂O | 0.31 |
| 15:3:12:10 | nBuOH:HOAc:H₂O:Pyridine | 0.45 |
| 1:1:1:1 | nBuOH:HOAc:H₂O:EtOAc | 0.60 |

EXAMPLE III $N^\alpha$-Succinoyl-Arginyl-Prolyl-Aspartyl-Valyl-Tyrosine

The peptide was prepared by the solid phase method, starting with BOC-TYr (BzlCl₂) resin ester (0.32 meg/g, 3.2 g). The following standard routines were used:

Deprotection—15 ml 50 percent TFA/CH₂Cl₂ for 1 min, then 15 ml 50 percent TFA/CH₂Cl₂ for 30 min;

Washing—15 ml CH₂Cl₂ twice for 1 min each, followed by 15 ml iPrOH for 1 min, then 15 ml CH₂Cl₂ twice for 1 min each;

Neutralization—15 ml 5 percent DIEA/CH₂Cl₂ twice for 2.5 min each;

Coupling—3.0 mmol of the protected amino acid (0.46 g) and HOBT were dissolved in 2 ml DMF and then diluted with 13 ml CH₂Cl₂. DCC (0.62 g) was dissolved in 3 ml CH₂Cl₂. The reaction mixture was agitated for 2 h.

In sequence, the resin was coupled once with BOC-Val, twice with BOC$^\alpha$-Bzl$^\beta$-Asp, and once each with BOC-Pro, AOC$^\alpha$-Tos$^g$-Arg and p-Anisyl succinate.

The resin was cleaved in HF/anisole (30 ml/7 ml) for 1 h at 0° C. The resin residue was quenched with Et₂O and filtered. The solids were extracted with 1 percent NH₄OH (100 ml) for 1 h, filtered and the extract lyophilized to give 0.88 g 3219-72HF, as a colorless brittle foam.

The crude peptide was purified on DEAE Sephadex (2.6×90 cm column, 0.33M NH₄HCO₃, pH 7.8 as elutent, 75 ml/h, 13 ml/fraction, 276 nm detector). Fractions 103-122 were pooled and lyophilized to give the desired compound as a colorless solid, 710 mg, 78 percent.

| Amino Acid Analysis: | | |
|---|---|---|
| Amino Acid | Ratio | |
| Arg | 1.01 | |
| Pro | 1.02 | |
| Asp | 0.99 | 82.7 percent peptide content |
| Val | 1.00 | |
| Tyr | 0.97 | |

| Thin Layer Chromatography: Silica Gel G, 250μ | | |
|---|---|---|
| Elutent | | $R_f$ |
| 3:1:1 | nBuOH:HOAc:H₂O | 0.51 |
| 15:3:12:10 | nBuOH:HOAc:H₂O:Pyridine | 0.54 |
| 1:1:1:1 | nBuOH:HOAc:H₂O:EtOAc | 0.61 |

EXAMPLE IV $N^\alpha$-Formyl-Arginyl-Prolyl-Aspartyl-Valyl-Tyrosine

The title compound was prepared by the solid phase method starting with BOC-Tyr(BzlCl₂) resin ester (0.32 meg/g, 4.7 g). The following standard routines were used:

Deprotection—25 ml 50 percent TFA/CH₂Cl₂ for 1 min, then 25 ml 50 percent TFA/CH₂Cl₂ for 30 min;

Washing—25 ml CH₂Cl₂ twice for 1 min. each, followed by 25 ml iPrOH for 1 min., then 25 ml CH₂Cl₂ twice for 1 min. each;

Neutralization—25 ml 5 percent DIEA/CH₂Cl₂ twice for 2.5 min each;

Coupling—4.5 mmol of the protected amino acid (0.69 g) and HOBT (0.46 g) were dissolved in 3 ml DMF and the diluted with 25 ml CH₂Cl₂ DCC (0.93 g) was dissolved in 5 ml CH₂Cl₂, added to the mixture of reactants and resin and agitated for 2 hr.

In sequence, the resin was coupled once with BOC-Val, BOC$^\alpha$-Bzl$^\beta$-Asp, BOC-Pro, and AOC$^\alpha$-Tos$^g$-Arg. The resin was then deprotected, neutralized and formylated with p-nitrophenyl formate (RC, 1.0 g), dimethylaminopyridine (0.3 g) in CH₂Cl₂ for 16 h.

The resin was washed, air-dried and cleaved with HF/anisole (30 ml/5 ml) for 1 h at 0° C. The resin residue was quenched with Et₂O and filtered. The solids were extracted with 1% NH₄OH (100 ml) and lyophilized to give 1.54 g of crude peptide.

The crude peptide was purified on DEAE Sephadex (2.6×85 cm column, 0.1M NH₄HCO₃, pH 7.5 as elutent, 100 ml/h flow rate, 13 ml fraction, 280 nm detection). Fractions 136-170 were collected and lyophilized to give the desired compound, 725 mg, 71%.

| Amino acid analysis: | | |
|---|---|---|
| Amino Acid | Ratio | |
| Arg | 1.04 | |
| Pro | 0.95 | |
| Asp | 1.01 | 100% peptide content |
| Val | 1.02 | |
| Tyr | 0.98 | |

| Thin Layer Chromatography: Silica Gel G, 250 | | |
|---|---|---|
| Elutent | | $R_f$ |
| 1:1 | Trifluoroethanol:NH₄OH | 0.64 |
| 15:3:12:10 | nBuOH:HOAc:H₂O:Pyridine | 0.50 |
| 1:1:1:1 | nBuOH:HOAc:H₂O:EtOAC | 0.60 |

EXAMPLE V $N^\alpha$-Acetyl-Arginyl-Prolyl-Aspartyl-Isoleucyl-Tyrosine, Solvated The title compound was prepared by the solid phase method, starting with BOC-Tyr(BzlCl₂) resin ester (0.32 meg/g, 2.4 g). The following standard routines were used:

Deprotection—20 ml 50 percent TFA/CH₂Cl₂ for 1 min, the 20 ml 50 percent TFA/CH Cl for 30 min;

Washing—20 ml CH₂Cl₂ twice for 1 min each, followed by 20 ml iPrOH for 1 min, then 20 ml CH₂Cl₂ twice for 1 min each;

Neutralization—20 ml 5 percent DIEA/CH₂Cl₂ twice for 2.5 min each;

Coupling—3.0 mmol of the protected amino acid (0.46 g) and HOBT were dissolved in 2 ml DMF and then diluted with 13 ml CH₂Cl₂. DCC (0.62 g) was dissolved in 3 ml CH₂Cl₂, added to the mixture of reactants and resin and agitated for 2 h.

In sequence, the resin was coupled once with BOC-Ile ½ H₂O, BOC$^\alpha$-Bzl$^\beta$-Asp, BOC-Pro, and AOC$^\alpha$-Tos$^g$-Arg.

After deprotection, the resin was acylated with Ac$_2$O (1.8 ml) and DMAP (0.3 g) in DMF (15 ml) for 2 h. The resin was washed, air-dried and cleaved in HF/anisole (30 ml/4 ml) for 1 h at 0° C.

The resin residue was quenched in Et$_2$O and filtered. The solids were extracted with 1 percent NH$_4$OH (100 ml) for 1 h, filtered and the extract lyophilized to give 2.1 g 3219-87 HF as a colorless solid.

The crude peptide was purified on DEAE Sephadex (2.6×85 cm column, 0.1M NH$_4$HCO$_3$, pH 7.5, 80 ml/h, 11 ml/fraction, 278 nm detector). Fractions 135-160 were pooled and lyophilized twice to give the desired compound as a colorless solid, 432 mg, 65 percent yield.

| Amino Acid Analysis: | | |
| --- | --- | --- |
| Amino Acid | Ratio | |
| Arg | 1.01 | |
| Pro | 1.02 | |
| Asp | 1.00 | 70.5 percent peptide content |
| Ile | 0.94 | |
| Tyr | 0.99 | |

| Thin Layer Chromatography 250µ, Silica Gel G | | |
| --- | --- | --- |
| | Elutent | R$_f$ |
| 1:1:1:1 | n-BuOH:HOAc:H$_2$O:EtOAc | 0.42 |
| 5:5:3:1 | EtOAc:Pyr:H$_2$O:HOAc | 0.49 |
| 15:3:12:10 | n-BuOH:HOAc:H$_2$O:Pyr | 0.53 |

EXAMPLE VI

N$^\alpha$-Acetyl-D-Arginyl-Prolyl-Aspartyl-Valyl-Tyrosine

The title compound was prepared as follows:

N-t-butyloxycarbonyl-Prolyl-($\beta$-benzyl)Aspartyl-Valyl-Tyrosine benzyl ester Into 100 ml methylene chloride and 50 ml saturated sodium bicarbonate solution was added 9.40 g ($\beta$-Bzl)Asp-Val-Tyr-OBzl trifluoroacetate. A small amount of dimethylformamide was added to dissolve the peptide. The layers were separated and the organic layer extracted with saturated sodium bicarbonate solution. The organic layer was dried over anhydrous sodium sulfate, then reduced in volume to about 50 ml by rotary evaporation. This solution was added to 2.80 g N-t-butyloxycarbonyl-Proline. The solution was chilled to 5° and 2.70 g dicylohexylcarbodiimide in 15 ml methylene chloride was added. The mixture was stirred at 5° for one hour, then let stand at 15° for 16 hours. The reaction mixture was reduced to a small volume by rotary evaporation. Ethyl acetate, 150 ml, was added to the residue and the mixture filtered. The filtrate was extracted with water, 10 percent citric acid solution, and saturated sodium bicarbonate solution. After drying, solvent removal left 10.97 g of a glass. The product was crystallized from ethyl acetate-hexane yielding 8.85 g, m.p. 74°-76°. Recrystallization from ethyl acetate—pet ether with only slight warming gave 7.73 g m.p. 75°-78°. TLC, silica gel 60: R$_f$ 0.68 with 9:1 CH$_2$Cl$_2$: MeOH.

N$^\alpha$-t-butyloxycarbonyl-(N$^g$-Tosyl)-D-Arginyl-Prolyl-($\beta$-benzyl) Aspartyl-Valyl-Tyrosine benzyl ester To 2.31 g BOC-Pro-($\beta$-Bzl)Asp-Val-TyrOBzl was added 20 ml 4.0N HCL in dioxane. After stirring one hour most of the solvent was removed by rotary evaporation. Addition of ether to the residue produced a solid which was filtered and washed with ether. The salt was combined with 1.20 g N-t-butyloxycarbonyl-(N$^g$-tosyl)-D-Arginine in 20 ml 3:1 methylene chloride-dimethylformamide. The solution was chilled to 5° and 0.61 ml diisopropylethylamine, 0.30 g 1-hydroxybenzotriazole, and 0.58 g dicycohexylcarbodiimide were added. The mixture was stirred at 5° for 30 minutes, then let stand at ambient temperature 16 hours. The reaction mixture was filtered and the solvent removed by rotary evaporation. To the residue was added ethyl acetate and water. The layers were separated and the organic layer extracted with 10 percent citric acid solution, saturated sodium bicarbonate solution, and saturated sodium chloride solution. Solvent removal left a glass which was crystallized from ethyl acetate—pet ether. The product came out of solution as a gum, but solidified to a white powder when triturated with pet ether. The product weighed 1.84 g.

N$^\alpha$-Acetyl-(N$^g$-tosyl)-D-Arginyl-Prolyl-($\beta$-benzyl) Aspartyl-Valyl-Tyrosine benzyl ester A 0.87 g portion of the protected pentapeptide was treated with 20 ml of 50 percent trifluoroacetic acid in methylene chloride for 30 minutes. Solvent removal and addition of ether to the residue produced a solid. The product was dissolved in 10 ml dimethylformamide, 0.15 ml diisopropylethylamine was added, followed by 0.5 ml acetic anhydride and 0.1 g 4-dimethylamino pyridine, and the mixture stirred 45 minutes. Most of the solvent was evaporated. To the residue was added 0.5N sodium bicarbonate solution; a creamy suspension resulted. Ethyl acetate was added and the organic layer extracted with water, 10 percent citric acid solution, and saturated sodium chloride solution. Solvent removal gave a gum weighing 0.69 g. This material was deprotected without purification. solvent was removed by rotary evaporation. Addition of ether to the residue produced a solid which was filtered and washed with ether. The salt was combined with 1.20 g N-t-butyloxycarbonyl-(N$^g$-tosyl)-D-Arginine in 20 ml 3:1 methylene chloride-dimethylformamide. The solution was chilled to 5° and 0.61 ml diisopropylethylamine, 0.30 g 1-hydroxybenzotriazole, and 0.58 g dicyclohexylcarbodiimide were added. The mixture was stirred at 5° for 30 minutes, then let stand at ambient temperature 16 hours. The reaction mixture was filtered and the solvent removed by rotary evaporation. To the residue was added ethyl acetate and water. The layers were separated and the organic layer extracted with 10 percent citric acid solution, saturated sodium bicarbonate solution, and saturated sodium chloride solution. Solvent removal left a glass which was crystallized from ethyl acetate—pet ether. The product came out of solution as a gum, but solidified to a white powder when triturated with pet ether. The product weighed 1.84 g.

N$^\alpha$-Acetyl-(N$^g$-tosyl)-D-Arginyl-Prolyl-($\beta$-benzyl) Aspartyl-Valyl-Tyrosine benzyl ester A 0.87 g portion of the protected pentapeptide was treated with 20 ml of 50 percent trifluoroacetic acid in methylene chloride for 30 minutes. Solvent removal and addition of ether to the residue produced a solid. The product was dissolved in 10 ml dimethylformamide, 0.15 ml diisopropylethylamine was added, followed by 0.5 ml acetic anhydride and 0.1 g 4-dimethylamino pyridine, and the mixture stirred 45 minutes. Most of the solvent was evaporated. To the residue was added 0.5N sodium bicarbonate solution; a creamy suspension resulted. Ethyl acetate was added and the organic layer extracted with water, 10 percent citric acid solution, and saturated sodium chloride solution. Solvent removal gave a gum weighing 0.69 g. This material was deprotected without purification.

N$^\alpha$-acetyl-D-Arginyl-Prolyl-Aspartyl-Valyl-Tyrosine

The 0.69 g protected peptide was placed in a teflon reaction vessel. M-cresol, 3 ml, and 30 ml HF were added and the mixture stirred at 0° for one hour. The HF was removed with vacuum. The peptide was precipitated with ethyl acetate-ether and washed with this solvent. The peptide was dissolved in 3 percent acetic acid and lyophilized. The product weighed 276 mg.

The peptide was purified by chromatography on a 1.6×60 cm column of DEAE-Sephadex eluted with 0.10N ammonium bicarbonate pH 8.0, collecting 120 drop fractions. The major component eluted with peak centered at fraction 82. The later half of the peak contained an impurity as shown by HPLC. Fractions 77-82 were combined and lyophilized. The product weighed 65 mg.

HPLC, Whatman $C_{18}$-Porasil: rt=8.8 min with 8 percent $CH_3CN$—0.01M $NH_4OAc$ pH 5 at 1.5 ml/min.

| $R_f$ | TLC, silica gel GF, 250 micron: | |
|---|---|---|
| | Solvent system | |
| 0.36 | 3:1:1 | nBuOH:HOAc:H$_2$O |
| 0.67 | 1:1:1:1 | n-BuOH:HOAc:H$_2$O:EtOAc |
| 0.55 | 15:3:12:10 | n-BuOH:HOAc:H$_2$O:pyr |

Amino acid analysis: Asp, 1.01; Pro, 0.99; Val, 0.99; Tyr, 1.01; Arg, 1.02; 100 percent peptide.

EXAMPLE VII

N$^\alpha$-acetyl-Arginyl-Prolyl-Aspartyl-Phenylalanyl-Tyrosine

The peptide was synthesized by the solid phase method on a Beckman 990B Automatic Peptide Synthesizer. Fifty percent trifluoroacetic acid-methylene chloride was used for deprotection, 5 percent diisopropylethylamine in $CH_2Cl_2$ for neutralization, and dicyclohexylcarbodiimide/1-hydroxybenzotriazole for coupling. The following starting materials were used: 2.00 g BOC-(Cl$_2$Bzl) Tyr-resin ester, 0.32 meq/g, 0.51 g BOC-Phe, 2×0.62 g BOC-($\beta$-Bzl)Asp, 0.42 g BOC-Pro, and 0.85 g AOC-(Ng-tosyl)Arg. After incorporation of Arg the resin was deprotected, neutralized, and reacted with 5 ml acetic anhydride in 20 ml dimethylformamide for 20 minutes. The resin was washed and dried; the weight was 2.73 g.

The peptide resin was treated with 30 ml HF and 3 ml m-cresol at 0 for 50 minutes. After evaporating the HF, the product was washed with ethyl acetate and ether. The peptide was extracted with 100 ml 5 percent acetic acid. The filtered solution was lyophilized yielding 798 mg crude product.

A 389 mg portion of the crude peptide was purified by chromatography on a 1.6×60 cm column of DEAE-Sephadex eluted with 0.10N NH$_4$HCO$_3$ pH 8.0. Fractions of 150 drops each were collected. Fractions 75-86 were combined and lyophilized. The product weighed 171 mg. HPLC showed only a trace of impurity, rt 8.2 min with 12.5 percent CH$_3$CN—0.01M NH$_4$OAc pH 5 at 2.0 ml per min on Whatman C$_{18}$-Porasil analytical column.

| $R_f$ | TLC, silica gel 60: | |
|---|---|---|
| | solvent system | |
| 0.21 | 3:1:1 | n-BuOH:HOAc:H$_2$O |
| 0.48 | 15:3:12:10 | n-BuOH:HOAc:H$_2$O:pyr |
| 0.59 | 1:1:1:1 | n-BuOH:HOAc:H$_2$O:EtOAc |

Amino acid analysis: Asp, 0.96; Pro, 1.00; Tyr, 1.01; Phe, 1.01; Arg, 1.02; 100 percent peptide.

EXAMPLE VIII

N$\alpha$-acetyl-Arginyl-Prolyl-Aspartyl-Glutaminyl-Tyrosine

The peptide was synthesized by the solid phase method. The resin was deprotected with 50 percent trifluroacetic acid in methylene chloride, neutralized with 5 percent diisopropylethylamine in methylene chloride, and coupled with dicyclohexylcarbodiimide and 1-hydroxybenzotriazole except for Gln which was incorporated via its p-nitrophenyl ester. The following starting materials were used: 2.00 g N-t-butyloxycarbonyl-(O-dichlorobenzyl) Tyrosine resin ester, 0.32 mequiv./g, 0.94 g N-t-butyloxycarbonyl-Glutamine p-nitrophenyl ester, 0.62 g N-t-butyloxycarbonyl-($\beta$-benzyl)Aspartic acid, 0.41 g N-t-butyloxycarbonyl-Proline, and 0.85 g N$^\alpha$-t-butyloxycarbonyl-(N$^g$-tosyl)-Arginine. Gln and Asp were recoupled. After incorporation of Arg, the resin was deprotected, neutralized, and reacted with 5 ml acetic anhydride and 1.25 ml diisopropylethylamine in 20 ml dimethyl formamide for 20 minutes. After washing, the resin was vacuum dried to give 2.75 g.

The peptide was cleaved with 30 ml HF and 3 ml m-cresol at 0° for one hour. The HF was removed with vacuum and the residue was washed with ethyl acetate and ether. The peptide was extracted with 150 ml 2 percent acetic acid. The filtered extract was lyophilized, yielding 688 mg product.

The peptide was purified by chromatography on a 2.6×90 cm column of DEAE-Sephadex eluted with 1.2L 0.10M ammonium bicarbnate pH 8.0, then 0.20M pH 8 buffer. The fractions of the major peak ($\lambda$278 nm) which were clean by HPLC were combined and lyophilized. The product weighed 388 mg.

| $R_f$ | TLC, silica gel 60: | |
|---|---|---|
| | solvent system | |
| 0.17 | 3:1:1 | n-BuOH:HOAc:H$_2$O |
| 0.31 | 15:3:12:10 | n-BuOH:HOAc:H$_2$O:pyr |
| 0.36 | 1:1:1:1 | n-BuOH:HOAc:H$_2$O:EtOAc |

Amino acid analysis: Asp, 0.99; Glx, 0.99; Pro, 1.03; Tyr, 0.98; Arg, 1.01; 100 percent peptide.

EXAMPLE IX

N$\alpha$-Acetyl-Arginyl-Prolyl-Aspartyl-Valyl-D-Tyrosine

The title compound was prepared as follows:

Boc-D-Tyr(2BrZ)-O-CH$_2$-Resin

Chloromethylated polymer (0.88 meq/g; 1.13 g; 1 mmol) and anhydrous KF (0.17 g; 3 mmol) were added to a solution of Boc-D-Tyr(2BrZ) (0.74 g; 1.5 mmol) in 4 ml of DMF in a round bottom flask equipped with an overhead stirrer. The reaction mixture was stirred at 50° C. for 24 hours. The resin was filtered and washed with DMF (3×25 ml), 50 percent DMF/H₂O (3×25 ml), 50 percent EtOH/H₂O (3×25 ml) and EtOH (3×25 ml). The substitution of Boc-D-Tyr(2BrZ) on the resin was 0.35 mmol per gram of resin based on amino acid analysis.

Aoc-Arg(Tos)-Pro-Asp-(OBzl)-Val-D-Tyr(2BrZ)-O-CH₂-Resin

Aoc-Arg(Tos)-Pro-Asp(OBzl)-Val-D-Tyr(2BrZ)-O-C H₂-Resin was synthesized manually by solid phase methodology. The amino acid derivatives and DCC were used in three fold excess with one equivalent of HOBt added for the following couplings: Aoc-Arg(Tos), Boc-Pro, Boc-Asp(OBzl) and Boc-Val. In addition to the DCC/HOBt couplings, symmetrical anhydride couplings had to be preformed to insure complete reaction for Boc-Val and Boc-Asp(OBzl). The anhydrides were formed prior to coupling by the addition of 1.5 eq DCC to 3 eq of the amino acid derivative at 0° for 1 hour. DCC was filtered off before addition to the resin-peptide. The following synthesis program was employed:
1. 50 percent TFA/CH₂Cl₂ (2 min., 15 min.)
2. CH₂Cl₂ (2×2 min.)
3. 50 percent TFA/CH₂Cl₂ (25 min.)
4. CH₂Cl₂ (3×2 min.)
5. isopropanol (2×1 min.)
6. CH₂Cl₂ (4×2 min.)
7. 7 percent DIEA/CH₂Cl₂ (1×3 min.); 2nd treatment (2 min., 5 min.)
8. CH₂Cl₂ (2×2 min.)
9. 7 percent DIEA/CH₂Cl₂ (3 min., 4 min.)
10. CH₂Cl₂ (5×2 min.)
11. Couple next amino acid in CH₂Cl₂.
12. Mix 5 min.
13. Add DCC and HOBt in CH₂Cl₂/DMF (10:1)
14. Mix overnight
15. CH₂Cl₂(6×2 min.)
16. Ninhydrin test (If incomplete reaction repeat steps 7-16)

The Aoc group of Arg was removed with 50 percent TA/CH₂Cl₂ prior to acetylation.

Ac-Arg(Tos)-Pro-Asp(OBzl)-Val-D-Tyr(2BrZ)-O-CH₂-Resin

TFA Arg(Tos)-Pro-Asp(OBzl)-Val-D-Tyr(2BrZ)-O-CH₂-R (~1 mmol) was stirred in a round bottomed flask with acetic anhydride (1.02 g; 10 mmol) for two hours at room temperature in 1:1 DMF/pyridine solution. The acetylated peptide-resin was transferred to a sintered glass funnel and washed with DMF. The product was dried in vacuo to yield 1.17 g of crude acetylated peptide-resin.

HF Cleavage

Ac-Arg(Tos)-Pro-Asp(OBzl)-Val-D-Tyr(2BrZ)-O-CH₂-Resin (1.17 g) was cleaved with 12 ml of HF in the presence of 10 percent anisole at 0° C. for 1 hour. The peptide resin was transferred into a sintered glass funnel and washed with ether thoroughly. The peptide was extracted with 10 percent HOAc/H₂O (5×10 ml) and then with H₂O and lyophilized to give 210 mg of peptide.

Purification of Ac-Arg-Pro-Asp-Val-D-Tyr

The crude Ac-Arg-Pro-Asp-Val-D-Tyr was chromatographed on a Sephadex SPC-25 column (2.5 cm×100 cm) equilibrated with 0.05M NH₄OAc (pH 4.5). The flow rate was 61 ml/hr and fractions of 12 ml/tube were collected. The UV monitor was set at λ=277 nm. The desired product eluted between tubes 23-28. The fractions were pooled and lyophilized to yield 140 mg of peptide (25 percent peptide).

Desalting of Ac-Arg-Pro-Asp-Val-D-Tyr

Since repeated lyophilization of the purified Ac-Arg-Pro-Asp-Val-D-Tyr failed to increase the peptide content, a Sephadex G-10 column (2.5 cm×100 cm) was used to desalt the peptide. The column was equilibrated in H₂O and was run with a flow rate of 30 ml/hr. Fractions of 10 ml/tube were collected with the UV monitor set at 207 nm for detection of the product. The peptide eluted between fractions 21-37. These fractions were pooled and lyophilized to yield 130 mg of a very hygroscopic material (33 percent peptide).

Thin layer chromatography (Silica Gel F60; 200 microns)
R$_f$ 0.43 (n-BuOH/HOAc/H₂O/pyr—15:3:12:10)
R$_f$ 0.60 (n-BuOH/HOAc/H₂O/EtOAC—1:1:1:1)

Amino acid analysis: Acid hydrolysis Asp, 0.99; Pro, 0.98; Val, 1.03; Tyr, 0.97; Arg, 1.02.

Leucine Amino Peptidase (LAP) Degradation Asp, 0.00; Pro, 0.00; Val, 0.00; Tyr, 0.00; Arg. 0.00; (0.00 means no liberated amino acids were detected).

EXAMPLE X

Nα-Acetyl-Arginyl-Prolyl-Aspartyl-Valyl-Tyrosine

The title compound was prepared by the solid phase method, starting with Boc-Tyr(BzlCl₂) resin ester (6.50 g, 0.32 meq/g). The following standard routines were used:

Deprotection—40 ml 50% TFA/CH₂Cl₂ for 1 min, then 40 ml 50% TFA/CH Cl for 30 min;
Washing—40 ml CH₂Cl₂ twice for 1 min each, followed by 40 ml iPrOH for 1 min, then 40 ml CH₂Cl₂ twice for 1 min each;
Neutralization—40 ml 5% DIEA/CH₂Cl₂ twice for 2.5 min each;
Coupling—6.0 mmol of the protected amino acid (0.92 g) and HOBT were dissolved in 3 ml DMF and then diluted with 27 ml CH₂Cl₂. DCC (1.24 g) was dissolved in 5 ml CH₂Cl₂, added to the mixture of reactants and resin and agitated for 2 h.

In sequence, the resin was coupled once each with Boc-Val, BOC-Bzlβ-Asp, and BOC-Pro. Half the resin was stored and the remainder coupled with Aocα-Tosᵍ-Arg. After deprotection, the resin peptide was acylated once with 10% Ac₂O in 1:1 DMF:CH₂Cl₂ (30 ml) and DMAP (400 mg) for 60 min. The resin was washed, air-dried and cleaved in HF/anisole (30 ml/8 ml) for 1 h at 0° C.

The resin residue was quenched in Et₂O and filtered. The solids were extracted with 10% HOAc (100 ml) for 1 h, filtered, and the extract lyophilized to give the product as a colorless solid.

The crude peptide was purified on QAE Sephadex (2.6×88 cm column, 41, 0.05 to 0.3M NH₄HCO₃ gradient, pH 7.2; 100 ml/h, 9 ml/fraction, 278 nm detector). Fractions 120-140 were pooled and lyophilized. The residue peptide was desalted on G-10 Sephadex (2.6×85 cm column, 1% HOAc as elutent). The lyophilized acetyl pentapeptide, weighed 830 mg.

Amino Acid Analysis:

-continued

| Amino Acid | Ratio | |
|---|---|---|
| Arg | 1.03 | |
| Pro | 0.99 | |
| Asp | 1.00 | 75.1% peptide content |
| Val | 1.00 | |
| Tyr | 0.97 | |

Thin Layer Chromatography 250μ Silica Gel G

| | Elutent | $R_f$ |
|---|---|---|
| 15:3:12:10 | n BuOH:HOAc:H₂O:Pyridine | 0.56 |
| 1:1:1:1 | n BuOH:HOAc:H₂O:EtOAc | 0.62 |
| 3:1:1 | n BuOH:HOAc:H₂O | 0.51 |

EXAMPLE XI

Arginyl-D-Prolyl-Aspartyl-Valyl-Tyrosine

The title compound was prepared as follows:

N-t-butyloxycarbonyl-D-Prolyl-(β-benzyl)Aspartyl-Valyl-Tyrosine benzyl ester To 4.00 g TFA (β-Bzl)Asp-Val-Tyr-OBzl (containing 15 percent excess TFA) was added 40 ml methylene chloride and 40 ml saturated sodium bicarbonate solution. The mixture was stirred vigorously, then the layers separated. The organic layer was extracted with bicarbonate solution, then dried. Solvent removal left a white solid. This material was dissolved in 45 ml 8:1 CH₂Cl₂:DMF. To the solution was added 1.08 g N-t-butyloxycarbonyl-D-Proline (Peninsula) and 0.1 g 1-hydroxybenzotriazole. The solution was chilled in an ice bath and 1.03 g dicyclohexylcarbodiimide was added. The mixture was stirred in the ice bath for 90 minutes and 90 minutes at ambient temperature. The precipitate was filtered. The filtrate was extracted with 10 percent citric acid solution, water and saturated sodium bicarbonate solution. Solvent removal left a glass which was crystallized from ethyl acetate-hexane. The product weighed 3.33 g, m.p. 82°–88° (d).

Tri-benzyloxycarbonyl-Arginyl-D-Prolyl(β-benzyl)Aspartyl-Valyl-Tyrosine benzyl ester To 3.31 g of the above protected tetrapeptide was added 40 ml 50 percent trifluoroacetic acid in methylene chloride. After stirring 30 min, the solvent was evaporated and ether added to the residue. The solid product was dissolved in ethyl acetate with addition of a small amount of methanol. The solution was extracted twice with saturated sodium bicarbonate solution. The solid from removal of the solvent from the organic layer was dissolved in 10 ml DMF and added to a solution of 2.77 g tribenzyloxycarbonyl-arginine (Bachem) in 5 ml DMF. The solution was chilled in an ice bath and 0.66 g 1-hydroxybenzotriazole was added, followed by 0.89 g dicyclohexylcarbodiimide. The reaction mixture was stirred at ambient temperature for 16 hours. Most of the solvent was removed with vacuum. Ethyl acetate was added to the residue and the insolubles filtered. The filtrate was extracted with 10 percent citric acid solution and twice with saturated sodium bicarbonate solution. Drying and solvent removal produced a thick oil product. This material was chromatographed on silica gel 60 with a gradient of 3–10 percent methanol in methylene chloride. A colorless glass product was obtained weighing 4.14 g.

Arginyl-D-Prolyl-Aspartyl-Valyl-Tyrosine

A 1.66 g portion of the protected pentapeptide was hydrogenated with 1 ml formic acid in 20 ml methanol over 0.5 g palladium black. After 4 hours of vigorous stirring, the catalyst was filtered and the solvent removed from the filtrate by rotary evaporation. The residue was dissolved in 5 percent aqueous acetic acid and lyophilized. The product weighed 889 mg.

The peptide was purified by chromatography on a 2.6×95 cm column of DEAE-Sephadex. Some material that did not dissolve in 0.25M NH₄HCO₃ pH 8.0 was filtered and the filtrate loaded onto the column. The column was eluted with this buffer at 100 ml/hour, collecting 10 ml fractions. The major component was collected in fractions 142–156. The lyophilized product weighed 634 mg.

HPLC: rt—6.5 min with 8 percent CH₃CN—0.01M NH₄OAc pH 5 at 1.5 ml/min on Whatman C₁₈-Porasil.

| TLC: silica gel GF, 250 micron | | |
|---|---|---|
| $R_f$ | | Solvent System |
| 0.42 | 1:1:1:1 | n-BuOH:HOAc:H₂O:EtOAc |
| 0.34 | 15:3:12:10 | n-BuOH:HOAc:H₂O:pyr |
| 0.53 | 1:1 | TFE:NH₄OH |

Amino acid analysis: Asp, 0.99; Pro, 0.98; Val, 1.01; Tyr, 1.00; Arg, 1.03; 94 percent peptide.

EXAMPLE XII

Nα-Acetyl-Arginyl-Prolyl-Aspartyl-Valyl-Tyrosine-N-Isobutylamide

The title compound was prepared as follows:

A. To a stirring solution of Pro-OCH₃·HCl (55.2 g, 33.3 mmol), Aoc$^α$-Tos$^g$-Arg (89.6 percent, 16.4 g, 33.3 mmol and 1-hydroxybenzotriazole (HOBT, 5.10 g, 33.3 mmol) in DMF (15 ml) and CH₂Cl₂ (50 ml) at 0° C. was added N-methylmorpholine (NMM, 385 ml, 1.1 eq). A solution of DCC (6.88 g, 1.0 eq) in CH₂Cl₂ (10 ml) was then added dropwise. After 5 min, the reaction was warmed to room temperature and stirred for 90 min. The resulting solids was filtered off and the filtrate evaporated to leave a yellow oil. This was suspended in EtOAc (200 ml) and refiltered. The solution was washed twice with saturated aqueous NaHCO₃, once with H₂O, once with 10 percent citric acid and once with saturated brine. The organic layer was dried over Na₂SO₄, filtered, and evaporated to give 17.90 g of a colorless foam. The reaction mixture was purified in 3 equal batches by flash chromatography (5×15 cm column, 5:3 CH₂Cl₂:acetone as elutent) to give methyl N$^g$-Tosyl-N$^α$-t-amyloxycarbonyl-arginyl-prolinate (product A) as a colorless glass, 13.41 g, 73 percent.

B. To a stirring solution of product A (5.54 g, 10.0 mmol) in CH₃OH (25 ml) at 5° C. was added chilled H₂O (20 ml) and 2.00M NaOH (aq) (5.00 ml, 10.0 mmol). The resulting colorless solution was maintained at 5°–10° C. for 18 h, and then warmed to room temperature for 1 h. The solution was evaporated to ca. 25 ml, the solution adjusted to pH 9.8 and extracted once with Et₂O. The aqueous residue was treated with solid citric acid to pH 2.8 and then saturated with NaCl. After extracting three times with EtOAc, the organic layers were combined, back-washed once with saturated brine, dried over Na₂SO₄, filtered and evaporated to give N$^g$-Tosyl-N$^α$-t-amyloxy-carbonyl-arginyl-proline (product B) as a colorless solid, 5.30 g, 98 percent, mp 114°–115° C.

C. To a stirring solution of BOC-Tyr(Brz) (4.94 g, 10.0 mmol) in EtOAc (40 ml) was added N-methylmorpholine (NMM, 1.21 ml, 1.1 eq). The solution was cooled to −20° C. and iBuOCOCl (1.33 ml, 1.02 eq) was added dropwise. After 20 min, isobutylamine (1.00 ml, 1.1 eq) was added. A thick, unstirrable mass formed after ca. 10 min. The reaction was warmed to room temperature, diluted with EtOAc (150 ml) and washed once with $H_2O$, once with 10 percent citric acid, once with $H_2O$, once with saturated aqueous $NaHCO_3$ and once with saturated brine. The organic layer was dried over $MgSO_4$, filtered and evaporated to give N-t-butyloxycarbonyl-O-(2-bromobenzyloxycarbonyl)-tyrosine-N-isobutylamide (product C) as a colorless solid sufficiently pure for further use, 5.10 g, 93 percent.

D. To product C (4.19 g, 7.63 mmol) was added 50 percent $TFA/CH_2Cl_2$ (14 ml). After stirring 40 min, the solution was evaporated at less than 30° C. and evacuated overnight to give product D1 as a yellow oil, 5.65 g.

To a stirring solution of BOC-Val (1.66, 1.00 eq) in EtOAC (24 ml) at −20° C. was added NMM (0.92 ml, 1.1 eq) and then, dropwise, iBuOCOCl (1.00 ml, 1.02 eq). After 20 min, a solution of product D1 and NMM (1.97 ml) in EtOAc (5 ml) was added and the reaction warmed to −5° C. After 30 min, a copious precipitate had formed. The reaction was quenched with $H_2O$ and extracted three times with EtOAc. The organic extracts were combined and washed once with saturated aqueous $NaHCO_3$, once with $H_2O$, once with 10 percent citric acid, and once with saturated brine. After drying over $MgSO_4$, the extract was filtered and evaporated. The resulting solid was triturated with hot $Et_2O$, filtered and dried to give N-t-butyloxycarbonyl-valyl-O-(2-bromobenzyloxycarbonyl)-tyrosine-N-isobutylamide (product D) as a colorless solid, 4.21 g, 85 percent, m.p. 175°–176° C.

E. To product D (1.95 g, 3.00 mmol) was added 4.5M HCl in dioxane (5 ml). After 1 h the solution was evaporated and the residue lyophilized from dioxane to give 1.60 g of a flocculant solid, product E1.

To a stirred solution of $N^\alpha$-BOC-$\beta$-Bzl-Asp (0.884 g, 1.0 eq) in DMF (5 ml) at −15° C. was added NMM (0.33 ml) and then iBuOCOCl (0.36 ml). After 15 min, a solution of product E1 and NMM (0.3 ml) in DMF (2 ml) was added, the reaction mixture was stirred and allowed to warm to room temperature. The tripeptide was precipitated with saturated aqueous $NaHCO_3$, washed with $H_2O$ and filtered. Recrystallization from EtOAc gave $N^\alpha$-t-butyloxycarbonyl-$\beta$-benzyl-aspartyl-valyl-O-(2-bromobenyloxycarbonyl)-tyrosine-N-isobutyl amide (product E) as a colorless solid, 1.90 g, 74 percent.

F. To product E (1.71 g, 2.00 mmol) was added 4.5M HCl in dioxane (3 ml). After 1 h, the solution was evaporated and the residue lyophilized from dioxane to give 1.46 g of a colorless solid. This was slurried in DMF (3 ml) and diisopropylethylamine (DIEA, 0.34 ml), HOBT (0.28 g) and $Aoc^\alpha$-$Tos^g$-Arg-Pro (product B) (0.98 g) were added. DCC (0.38 g) was then added and the reaction stirred for 2 h. The slurry was filtered and the filtrate quenched with half-saturated aqueous $NaHCO_3$ (50 ml). The resulting solids were filtered, taken up in EtOAc and washed with $H_2O$, 10 percent citric acid and saturated brine. The organic phase was dried over $Na_2SO_4$, filtered and evaporated to give $N^\alpha$-t-amyloxycarbonyl-$N^g$-tosyl-arginyl-prolyl-$\beta$-benzyl-aspartyl valyl-O-(2-bromobenzyloxycarbonyl)-tyrosine-N-isobutylamide (product F) as a pale yellow solid, 1.91 g, 75 percent.

G. To product F (1.85 g, 1.45 mmol) was added 50 percent $TFA/CH_2Cl_2$ (4 ml). After 30 min, the solution was evaporated in the cold and triturated with $Et_2O$ to give a colorless solid, 2.35 g. To this solid was added NMM (0.64 ml), DMAP (0.12 g) and DMF (5 ml). $Ac_2O$ (0.5 ml) was then added and the resulting deep yellow solution was stirred for 1 h. The reaction was quenched with half-saturated $NaHCO_3$ solution. The resulting tan precipitate was collected, washed with 10 percent citric acid, $H_2O$, and air-dried to give $N^\alpha$-acetyl-$N^g$-tosyl-arginyl-prolyl-$\beta$-benzyl-aspartyl-valyl-O-(2-bromobenzyloxycarbonyl)-tyrosine-N-isobutyl amide (product G) 1.34 g, 77 percent.

H. The protected pentapeptide product G (1.34 g) was cleaved with HF/anisole (30 ml/6 ml) for 1 h at 0°. The residue was quenched with $Et_2O$ and extracted once with 10 percent HOAc (100 ml) and once with 1 percent $NH_4OH$ (100 ml). The aqueous extracts were combined and lyophilized to give a yellow solid, 0.65 g.

The crude peptide was purified on SPC25 Sephadex (2.6×90 cm column, 0.8M pH 4.8 $Et_3NHOAc$ elutent, 70 ml/hr flow rate, 8 ml/fraction, 278 nm detector). Fractions 91–114 were collected and lyophilized to give the title compound 285 mg as a colorless solid.

| Amino Acid Analysis: | | |
|---|---|---|
| Amino Acid | Ratio | |
| Arg | 1.01 | |
| Pro | 1.02 | |
| Asp | 1.01 | 57.4 percent peptide content |
| Val | 1.00 | |
| Tyr | 0.95 | |

| Thin Layer Layer Chromatography: Silica Gel G, 250μ | | |
|---|---|---|
| | Elutent | $R_f$ |
| 15:3:12:10 | nBuOH:HOAc:$H_2O$:Pyridine | 0.67 |
| 1:1 | Trifluoroethanol:$NH_4OH$ | 0.90 |
| 1:1:1:1 | nBuOH:HOAc:$H_2O$:EtOAc | 0.67 |

EXAMPLE XIII

Nα-Acetyl-Arginyl-Prolyl-Aspartyl-Alanyl-Tyrosine

The title compound was prepared by the solid phase method, starting with BOC-Tyr(BzlCl₂) resin ester (0.32 meq/g, 3.2 g). The following standard routines were used:

Deprotection—15 ml 50 percent $TFA/CH_2Cl_2$ for 1 min, then 15 m 50 percent $TFA/CH_2Cl_2$ for 30 min;

Washing—15 ml $CH_2Cl_2$ twice for 1 min each, followed by 15 ml iPrOH for 1 min, then 15 ml $CH_2Cl_2$ twice for 1 min each;

Neutralization—15 ml 5 percent $DIEA/CH_2Cl_2$ twice for 2.5 min each;

Coupling—3.0 mmol of the protected amino acid (0.46 g) and HOBT were dissolved in 2 ml DMF and then diluted with 13 ml $CH_2Cl_2$. DCC (0.62 g) was dissolved in 3 ml $CH_2Cl_2$, added to the mixture of reactants and resin and agitated for 2 h.

In sequence, the resin was coupled once with BOC-Ala, $BOC^\alpha$-$Bzl^\beta$-Asp, BOC-Pro, and $AOC^\alpha$-$Tos^g$-Arg. After deprotection, the resin peptide was acylated twice with 14 percent $Ac_2O$ in $CH_2Cl_2$ and DMAP (60 mg) for 30 min.

The resin was cleaved with HF/anisole (40 ml/10 ml) for 1 h at 0° C. The resin was quenched with $Et_2O$ and filtered. The solids were extracted in 100 ml 10 percent HOAc for 1 h, filtered and the filtrate lyophilized to give crude product 1.08 g.

The crude peptide was purified on a DEAE Sephadex (2.6×90 cm column, 0.1M NH$_4$HCO$_3$ pH 7.8 as elutent, 70 ml/hr flow rate, 6.5 ml/fraction, 280 nm detection). Fractions 175–220 were collected and lyophilized to give the title compound, 650 mg, 55 percent.

| Amino Acid Analysis: | | |
|---|---|---|
| Amino Acid | Ratio | |
| Arg | 1.01 | |
| Pro | 1.02 | |
| Asp | 1.00 | 55.9 percent peptide content |
| Ala | 0.98 | |
| Tyr | 0.98 | |

| Thin Layer Chromatography: Silica Gel G. 250μ | | |
|---|---|---|
| | Elutent | R |
| 15:3:12:10 | nBuOH:HOAc:H$_2$O:Pyridine | 0.49 |
| 4:1:5 | nBuOH:HOAc:H$_2$O, upper phase | 0.23 |
| 1:1:1:1 | nBuOH:HOAc:H$_2$O:EtOAc | 0.59 |

EXAMPLE XIV

Arginyl-α-aminoisobutyryl-Aspartyl-Valyl-Tyrosine

The title product was prepared as follows:

N-t-butyloxycarbonyl-α-aminoisobutyryl-(β-benzyl)-Asparytl-Valyl-Tyrosine benzyl ester The free amine was obtained from 2.10 g (β-Bzl)Asp-Val-TyrOBzl trifluoroacetate by neutralization with aqueous base and extraction into ethyl acetate. Solvent removal gave 1.90 g solid which was dissolved in 25 ml methylene chloride with the addition of 0.49 g 1-hydroxybenzotriazole in 5 ml DMF. The solution was chilled to 5° and 0.65 g N-t-butyloxycarbonyl-α-aminoisobutyric acid was added, followed by 0.66 g dicyclohexylcarbodiimide. The mixture was stirred at 5° thirty minutes, then let stand at ambient temperature 16 hours. The reaction mixture was filtered and the filtrate extracted with water, then diluted with methylene chloride and extracted twice with saturated sodium bicarbonate solution. After drying over anhydrous magnesium sulfate, solvent removal left an oil which was purified by flash chromatography on silica gel 60 eluted first with 1 percent methanol in methylene chloride, then 5 percent MeOH—CH$_2$Cl$_2$. The major product, a colorless glass, weighed 1.75 g.

N$^{\alpha,\delta,\omega}$-tribenzyloxycarbonyl-Arginyl-α-aminoisobutyryl-(β-benzyl)-Aspartyl-Valyl-Tyrosine benzyl ester To 1.75 g BOC-Aib-(β-Bzl)-Asp-Val-TyrOBzl was added 25 ml 4.5N HCl in dioxane and the solution was stirred 50 minutes. The volume was reduced by rotary evaporation and ether was added to the residue. The precipitate was filtered and washed with ether. The free amine was obtained from the salt by neutralization with aqueous base and extraction into methylene chloride. Solvent removal left 1.36 g colorless glass.

The tetrapeptide was dissolved in 10 ml methylene chloride and added to a solution of 1.27 g N$^{\alpha,\delta,\omega}$-tribenzyloxycarbonyl-arginine and 0.34 g 1-hydroxybenzotriazole in 5 ml DMF. The solution was cooled in an ice bath and a solution of 0.45 g dicylohexylcarbodiimide in 5 ml CH$_2$Cl$_2$ was added. The mixture was stirred in the ice bath for 30 minutes, then at room temperature for 3½ hours. The reaction mixture was diluted with methylene chloride and filtered. The filtrate was extracted with water, twice with saturated sodium bicarbonate solution, 10 percent citric acid solution, and saturated sodium chloride solution. After drying, the solvent was evaporated leaving an oil. The product was purified by flash chromatography on silica gel 60 with 98:2 CH$_2$Cl$_2$:MeOH elution. The major product was a gum weighing 2.06 g. The NMR spectrum was correct for Z$_3$-Arg-Aib-(β-Bzl)-Asp-Val TyrOBzl and indicated the product to be a DMF solvate, 3 mols per mol of peptide.

Arginyl-α-aminoisobutyryl-Aspartyl-Valyl-Tyrosine

The 1.75 g protected pentapeptide was hydrogenated with 40 psi hydrogen over 10 percent palladium on carbon, using 9:1 methanol-1N aqueous acetic acid as the solvent. After shaking 18 hours on a Parr apparatus, the mixture was filtered, and the catalyst was washed with water. The methanol was removed from the filtrate with reduced pressure. The residue was diluted with 5 percent acetic acid and lyophilized. The product weighed 687 mg.

The peptide was purified by chromatography on a 2.6×90 cm column of SP-Sephadex eluted with 0.1N ammonium acetate pH 5. Some material that was insoluble in this buffer was filtered before loading the solution onto the column. The major component eluted in fractions 70–92 (10 ml each). The HPLC pure fractions, 78–92, were combined and lyophilized yielding 725 mg of the title compound.

| | TLC, silica gel 60: | |
|---|---|---|
| R$_f$ | | Solvent System |
| 0.32 | 1:1:1:1 | n-BuOH:HOAc:H$_2$O:EtOAc |
| 0.33 | 15:3:12:10 | n-BuOH:HOAc:H$_2$O:pyr |
| 0.13 | 3:1:1 | N-BuOH:HOAc:H$_2$O |

Amino acid analysis: Asp, 0.99; Val, 1.01; Tyr, 1.00; Arg, 1.02; Aib, 1.01; 57.7 percent peptide.

EXAMPLE XV

Nα-Acetyl-Arginyl-Prolyl-Aspartyl-Valyl-Tyrosine-N-Methylamide

The title compound was prepared as follows:

A. Boc-Val-Tyr-NHCH$_3$.

A 500 ml 3-necked round-bottomed flask was fitted with a gas-inlet tube and a dry-ice-cooled cold finger condenser with drying tube. The flask was charged with Boc—Val—Tyr—OBzl (6.95 g, 14.8 mmol) and Et$_2$O (250 ml). Methylamine (ca. 20 g) was bubbled into the stirred slurry. A colorless solution quickly formed. After 1 h, the flask was stoppered and stored at room temperature for 101 h. The resulting solids were filtered, and the supernatant solution evaporated to dryness. The combined solids were trituated in hot EtOAc, filtered and air-dried to give Boc-Val-Tyr-NHCH$_3$, (product A) 5.03 g, 86%.

B. Boc-(Bzl$^\beta$)Asp-Val-Tyr-NHCH$_3$.

To a stirred solution of 4.5M HCl-dioxane (7 ml) was added product A (2.75 g, 7.00 mmol). After 1 h, the solution was evaporated at reduced pressure. The residue was dissolved in H$_2$O and lyophilized to give HCl.Val-Tyr-NHCH$_3$ (product B1) 2.28 g, 99%.

To a stirred solution of product B1 (2.28 g, 6.91 mmol) and Boc-(Bzl$^\beta$)-Asp succinimide ester (2.90 g, 6.90 mmol) in DMF (5 ml) was added N-methylmorpholine (NMM, 0.85 ml). The resulting faintly yellow solution was stirred 24 h and then quenched with 5% citric acid (150 ml). The solids were collected, washed with saturated aqueous NaHCO₃, H₂O and Et₂O. The light yellow solid was air-dried and recrystallized from EtOAc/CH₃OH to give product B 3.45 g, 84%.

C. Boc-Pro-(Bzlβ)Asp-Val-Tyr-NHCH₃.

To a stirred solution of 4.5M HCl in dioxane (10 ml) was added product B (2.80 g, 4.68 mmol). After 1 h, the solution was evaporated at reduced pressure. The residue was dissolved in H₂O and lyophilized to give HCl.(Bzlβ) Asp-Val-Tyr-NHCH₃, (product C1) 2.36 g, 92%.

To a stirred solution of product C1 (2.31 g, 4.32 mmol) and Boc—Pro-hydroxysuccinimide ester (1.35 g, 4.32 mmol) in DMF (10 ml) was added NMM (0.55 ml). This solution was stirred 22 h and then quenched with saturated aqueous NaHCO₃. The solids were collected, washed with H₂O, 10% citric acid and H₂O. The light yellow solid was air-dried and recrystallized from EtOAc to give product C 2.32 g, 77%.

D. HCl.(NO₂$^g$)Arg-Pro-(Bzlβ)Asp-Val-Tyr-NHCH₃.

To a stirred solution of 4.5M HCl. dioxane (5 ml) was added product C (2.02 g, 2.90 mmol). A precipitate formed after about 10 min. After 1 h, the slurry was evaporated at reduced pressure. The residue was dissolved in H₂O and lyophilized to give HCl.Pro-(Bzlβ)Asp-Val-Tyr-NHCH₃, (product D1) 1.75 g, 95%, as a colorless powder.

To a stirred solution of product D1 (1.73 g, 2.74 mmol), (BOC$^α$-NO₂$^g$)Arg (87.9%, 0.99 g, 2.73 mmol), 1-hydroxybenzotriazole (HOBT, 0.42 g) and NMM (0.33 ml) in DMF (5 ml) was added dicyclohexylcarbodiimide (DCC, 0.56 g). A precipitate formed after 5 min. After 3 h, the reaction mixture was filtered and the filtrate treated with saturated aqueous NaHCO₃. The resulting solids were collected, washed with H₂O, 10% citric acid, and H₂O. The colorless solid was air-dried and triturated in hot EtOAc, to give Boc(NO₂$^g$)Arg-Pro-(Bzlβ)-Asp-Val-Tyr-NHCH₃ (product D2) 2.04 g, 83%.

To a stirred solution of 4.5M HCl in dioxane (5 ml) was added product D2 (1.92 g). After 1 h, the pasty reaction mixture was evaporated at reduced pressure. The residue was dissolved in H₂O and lyophilized to give product D, 1.64 g, 92%.

E. Ac$^α$-Arg-Pro-Asp-Val-Tyr-NHCH₃.

To a stirred solution of product D (1.61 g, 1.93 mmol) and N-acetoxy-succinimide (0.33 g) in DMF (5 ml) was added DIEA (0.71 ml). After 3 h, the mixture was evaporated under reduced pressure. After treating the residue with H₂O and decanting, the resulting solid was dissolved in 50% aqueous HOAc (100 ml). After purging the solution with N₂, 0.5 g 10% Pd/C was added and the mixture subjected to hydrogenation on a Parr apparatus (500 ml vessel, P₀=47.0 psig). After.68 h, the reaction mixture was filtered through a Micropore filter, evaporated at reduced pressure, dissolved in H₂O and lyophilized. The resulting crude residue (product E1) weighed 1.21 g.

The crude acylated pentapeptide was initially purified on Sephadex SPC-25 (2.6×85 cm column, 0.05M NH₄OAc, pH 4.5, 100 ml/h flow rate, 10 ml/fraction). Fractions 38–75 were pooled and lyophilized to give 3219-18201, 600 mg. Because of low purity (92% by HPLC), half of this was re-chromatographed on Sephadex DEAE (2.6×81 cm column, 0.03M NH₄HCO₃, pH 8.9, 100 ml/h flow rate, 10 ml/fraction). Fractions 40–50 were pooled and lyophilized to give the title compound, 375 mg, 49%.

| Amino Acid Analysis: | | |
|---|---|---|
| Amino Acid | Ratio | |
| Arg | 0.99 | |
| Pro | 1.01 | |
| Asp | 1.03 | 89.2% peptide |
| Val | 1.01 | |
| Tyr | 0.97 | |

| Thin Layer Chromatography: | | |
|---|---|---|
| | Elutent | $R_f$ |
| 15:3:12:10 | n-BuOH:HOAc:H₂O:Pyridine | 0.53 |
| 1:1:1:1 | n-BuOH:HOAc:H₂O:EtOAc | 0.19 |
| 3:1:1 | n-BuOH:HOAc:H₂O | 0.17 |

EXAMPLE XVI

N$^α$-Acetyl-Arginyl-Prolyl-Glutamyl-Valyl-Tyrosine amide

The title compound was prepared by the solid phase method, starting with p-methylbenzhydrylamine resin (U.S. Biochemical 31578, 4.0 g, 0.25 meg/g). The following standard routines were used:

Deprotection—30 ml 50% TFA/CH₂Cl₂ for 1 min, then 30 ml 50% TFA/CHCl for 30 min;

Washing—30 ml CH₂Cl₂ twice for 1 min each, followed by 30 ml iPrOH for 1 min, then 30 ml CH₂Cl₂ twice for 1 min each;

Neutralization—30 ml 5% DIEA/CH₂Cl₂ twice for 2.5 min each;

Coupling—3.0 mmol of the protected amino acid (0.46 g) and HOBT were dissolved in 3 ml DMF and then diluted with 27 ml CH₂Cl₂. DCC (0.62 g) was dissolved in 5 ml CH₂Cl₂, added to the mixture of reactants and resin and agitated for 2 h.

In sequence, the resin was coupled once with BOC-Val, BOC-Bzlγ-Glu, BOC-Pro, and AOC$^α$-Tos$^g$-Arg. After deprotection, the resin peptide was acylated once with 10 percent Ac₂O in 1:1 DMF:CH₂Cl₂ and DMAP (60 mg) for 60 min. The resin was washed, air-dried and cleaved in HF/anisole (30 ml/8 ml) for 1 h at 0° C.

The resin residue was quenched in Et₂O and filtered. The solids were extracted with 0.3% NH₄OH (100 ml) for 1 h, filtered, and the extract lyophilized to give crude peptide as a colorless solid, 378 mg.

The crude peptide was first purified on SPC25 Sephadex (2.6×83 cm column, 0.03M pH 4.5 NH₄OAc, 75 ml/h, 10 ml/fraction, 278 nm detector). Fractions 140–172 were pooled and lyophilized to give a lyophilate.

The lyophilate was re-chromatographed on DEAE Sephedex (2.6×89 cm column, 0.03M pH 8.9 NH₄OAc, 75 ml/h, 10 ml/fraction, 278 nm detector). Fractions 36–46 were pooled and lyophilized to give the title compound 210 mg.

| Amino Acid Analysis | | |
|---|---|---|
| Amino Acid | Ratio | |
| Arg | 1.00 | |
| Pro | 1.02 | |
| Glu | 1.02 | 92.2% peptide content |
| Val | 0.99 | |
| Tyr | 0.98 | |

| Thin Layer Chromatography 250μ Silica Gel G | |
|---|---|
| Elutent | $R_f$ |

-continued

| | | |
|---|---|---|
| 15:3:12:10 | n-BuOH:HOAc:H₂O:Pyridine | 0.53 |
| 1:1:1:1 | n-BuOH:HOAc:H₂O:EtOAc | 0.33 |
| 5:5:3:1 | EtOAc:H₂O:Pyr:HOAc | 0.72 |

EXAMPLE XVII $N^\alpha$-acetyl-D-Arginyl-Prolyl-Aspartyl-Valyl-Tyrosine Amide The title peptide was synthesized by the solid phase method on a Beckman 990B Automatic Peptide Synthesizer. The synthesis was started with 4.00 g p-methylbenzhydrylamine resin, substitution level 0.25 mmol per gram. Fifty percent trifluoroacetic acid in methylene chloride was used in the deprotection step, 5 percent diisopropylethylamine in $CH_2Cl_2$ in the neutralization step, and DCC-HOBt in the coupling step. The following amino acid derivatives were sequencially coupled to the resin: BOC-Tyr(BrZ), BOC-Val, BOC-Asp($\beta$-Bzl), BOC-Pro, and BOC-D-Arg ($N^g$-tosyl). After incorporation of D-Arg, the resin was deprotected, neutralized, and reacted with acetic anhydride in dimethylformamide with 4-dimethylpyridine as a catalyst. The resin was washed and dried with vacuum. The dried resin weighted 5.15 g.

The peptide was cleaved from the resin with 50 ml HF containing 5 ml m-cresol at 0° for one hour. After vacuum removal of the HF, the residue was washed with ethyl acetate and ether. The peptide was extracted with 100 ml 5 percent aqueous acetic acid. The extract was lyophilized, yielding 658 mg crude peptide.

The peptide was purified by chromatographing twice on ion exchange resin. The first elution was on a 2.6×100 cm column of DEAE-Sephadex with 0.05M $NH_4HCO_3$ pH 8.0. Fractions 57–66 (10 ml each) were combined and lyophilized. The 572 mg product was loaded onto 2.6×90 cm column of SP-Sephadex and eluted with 0.02M $NH_4OAc$ pH 4.6. Fractions of 7.5 ml were collected. The major peak was divided into three cuts: fractions 190–215, 216–240, and 241–285. The lyophilized yield and purity (HPLC) of these cuts were: 48 mg (98.8 percent), 107 mg (98.4 percent), 232 mg (97.3 percent).

| TLC, silica gel 60: | | |
|---|---|---|
| R_f 0.19 | 3:1:1 | n-BuOH:HOAc:H₂O |
| R_f 0.44 | 15:3:12:10 | n-BuOH:HOAc:H₂O:pyr |
| R_f 0.81 | 3:2:1 | pyr:HOAc:H₂O |

Amino Acid analysis: Asp, 0.99; Pro, 1.02; Val, 1.03; Tyr, 0.96; Arg, 1.01; 80.5 percent peptide

EXAMPLE XVIII $N\alpha$-Acetyl-Arginyl-$\alpha$-Aminoisobutyryl-Aspartyl-Valyl-Tyrosine amide The title compound was prepared by the solid phase method, starting with p-methylbenzhydrylamine resin (U.S. Biochemical 31578, 6.83 g, 0.3 meq/g). The following standard routines were used:

Deprotection—50 ml 50% TFA/CH₂Cl₂ for 1 min, then 50 ml 50% TFA/CHCl for 30 min;
Washing—50 ml CH₂Cl₂ twice for 1 min each, followed by 50 ml iPrOH for 1 min, then 50 ml CH₂Cl₂ twice for 1 min each;
Neutralization—50 ml 5% DIEA/CH₂Cl₂ twice for 2.5 min each;
Coupling—5.0 mmol of the protected amino acid and HOBT (0.77 g) were dissolved in 4 ml DMF and then diluted with 41 ml CH₂Cl₂. DCC (1.03 g) was dissolved in 5 ml CH₂Cl₂, added to the mixture of reactants and resin and agitated for 2 h.

In sequence, the resin was coupled once with BOC-Val, BOC-Bzl$\beta$-Asp, BOC-Aib, and twice with AOC$\alpha$-Tos$g$-Arg. After deprotection, half of the resin peptide was acylated once with 10 percent $Ac_2O$ in 1:1 DMF:CH₂Cl₂ (30 ml) and DMAP (400 mg) for 60 min. The resin was washed, air-dried and cleaved in HF/anisole (30 ml/8 ml) for 1 h at 0° C.

The resin residue was quenched in Et₂O and filtered. The solids were extracted with 1% NH₄OH (100 ml) for 1 h, filtered, and the extract lyophilized to give crude peptide as a colorless solid, 425 mg.

The crude peptide was purified on DEAE Sephadex (2.6×85 cm column, 0.03M NH₄HCO₃, unbuffered; 75 ml/h, 7 ml/fraction, 278 nm detector). Fractions 79–95 were pooled and lyophilized to give the title compound, 260 mg.

| Amino Acid Analysis | | |
|---|---|---|
| Amino Acid | Ratio | |
| Arg | 1.02 | |
| Aib | 0.89 | |
| Asp | 1.00 | 84.8% peptide content |
| Val | 1.02 | |
| Tyr | 1.00 | |

| Thin Layer Chromatography 250μ Silica Gel G | | |
|---|---|---|
| | Elutent | R_f |
| 15:3:12:10 | n-BuOH:HOAc:H₂O:Pyridine | 0.61 |
| 1:1:1:1 | n-BuOH:HOAc:H₂O:EtOAc | 0.57 |
| 4:2:3:1 | n-BuOH:HOAc:H₂O:Pyridine | 0.71 |

EXAMPLE XIX

Arginyl-$\alpha$-Aminoisobutyryl-Aspartyl-Valyl-Tyrosine amide

The title compound was prepared by the solid phase method as described in Example XVIII. The remaining resin was washed, air-dried and cleaved in HF/anisole (30 ml/8 ml) for 1 h at 0° C.

The resin residue was quenched in Et₂O and filtered. The solids were extracted with 10% HOAc (100 ml) filtered, and the extract lyophilized to give crude peptide as a colorless solid, 385 mg.

The crude peptide was purified on CM Sephadex (2.6×80 cm column, 21 0.10M unbuffered, NH₄OAc then 0.2M NH₄OAc, 75 ml/h, 12 ml/fraction, 278 nm detector).

Fractions 62–99 were pooled and lyophilized to give the title compound, 435 ml, 50% yield.

| Amino Acid Analysis | | |
|---|---|---|
| Amino Acid | Ratio | |
| Arg | 1.02 | |
| Aib | 0.95 | |
| Asp | 0.97 | 58.3% peptide content |
| Val | 1.01 | |
| Tyr | 1.00 | |

| Thin Layer Chromatography 250μ Silica Gel G | | |
|---|---|---|
| | Elutent | R_f |
| 15:3:12:10 | n-BuOH:HOAc:H₂O:Pyridine | 0.55 |

| | | |
|---|---|---|
| 1:1:1:1 | n-BuOH:HOAc:H₂O:EtOAc | 0.56 |
| 4:2:3:1 | n-BuOH:HOAc:H₂O:Pyridine | 0.72 |

EXAMPLE XX

Nα-Acetyl-Arginyl-3,4-dehydro-Propyl-Aspartyl-Valyl-Tyrosineamide

The title compound was prepared as follows:

BOC-3,4-dehydro-Proline 3,4-dehydro-Pro (200 mg; 1.76 mmoles) was dissolved in dioxane/H₂O (8 ml; 2:1). To this solution, 1N NaOH (1.8 ml) and di-t-butyldicarbonate (436 mg; 2 mmoles) were added at 0° C. with stirring. The mixture was then stirred at room temperature overnight. Dioxane was removed and to the remaining water phase, ethyl acetate (20 ml) was added. The mixture was cooled in an ice bath, acidified to pH 2.0 with 0.5N HCl and transferred into separation funnel. The oganic layer was separated and the aqueous layer was extracted twice with EtOAc (2×20 ml). The combined organic phase was dried over Na₂SO₄ and filtered. The solvent was removed and the remaining residue was dried and used without further purification.

Nα-Acetyl-Arginyl-3,4-dehydro-Prolyl-Aspartyl-Valyl-Tyrosineamide

The peptide was synthesized on a (p-methyl)benzhydrylamine-resin (2 g resin; substitution of 0.25 mmoles of NH₂ of g resin) by solid-phase method. The incorporation of BOC-Tyr-(Bzl), BOC-Val, BOC-3,4-dehydro-Pro and Aoc-Arg(Tos) was carried out via DCC-coupling. The coupling was monitored by qualitative ninhydrin test. The acetylation of arginine was carried out with 50 percent acetic anhydride/pyridine (15 ml) and DMAP (15 mg). The peptidyl resin was then washed thoroughly with DMF and CH₂Cl₂ and dried. The dried peptidyl resin (2 g) was cleaved with HF/anisole (20 ml; 9:1) at 0° C. for 1 h. The peptide-resin mixture was washed with ether (3×20 ml). After lyophilization, the peptide was applied onto a Sephadex SPC-25 column (50 cm×0.9 cm) and equilibrated with 0.02M NH₄OAc; pH 4.6. The flow rate was 80 ml/hr and fractions of 12 ml were collected. The product was eluted between tubes 22–39, which were pooled and lyophilized.

The lyophilized material was purified again on Sephadex SPC-25 column (60 cm×2.5 cm) equilibrated with 0.02M NH₄OAc; pH 4.5–6.8 under the same condition as described above. The peptide was eluted between tubes 55–75, which were pooled and lyophilized to give 80 mg of the title product.

Rf 0.45 (n-BuOH/HOAc/H₂O/Pyr 15:3:12:10; Silica Gel F60)

Rf 0.27 (n-BuOH/HOAc/H₂O 3:1:1; Silica Gel F60)

Amino Acid Analysis: Asp, 1.04; Val, 1.00; Tyr, 0.85; Arg, 0.96; 3,4-dehydro-Pro, 1.08 Peptide content: 72 percent; hygroscopic material 3,4-dehydro-Pro eluted next to Asp-residue in the Analysis and has a very low KF-value.

HPLC: Whatman Partisil—ODS column. 10 percent CH₃CN/0.02M NH₄OAc; pH 4.6. Flow rate: 2 ml/min.

The peptide was 99.7 percent pure and has a retention time of 14.3 min.

EXAMPLE XXI

Arginyl-Prolyl-Aspartyl-Valyl-Tyrosinamide

The title compound was prepared as follows:

Z—Arg(Z,Z)-Pro-Asp(OBzl)-Val-Tyr-NH₂

To a solution of HCl Pro-Asp(OBzl)-Val-Tyr-NH₂ (0.5 g; 0.7 mmoles) in DMF (15 ml), DIEA (0.14 ml; 0.7 mmoles) and Z-Arg(Z,Z)-ONp (0.7 g; 1 mmoles) were added at 0° C. with stirring. The mixture was stirred at room temperature over weekend. The solvent was removed on rotavapor. The residue was triturated with ether and filtered. The solid was recrystallized from CH₃OH and CH₂Cl₂/ether/pet ether mixture to give 0.59 g of product; Rf 0.78 (n-BuOH/HOAc/H₂O=3:1:1; Silica Gel; 200 microns); ¹H-NMR (DMSO-d₆) indicated the presence of Z-Arg(Z,Z)-moiety.

Arg-Pro-Asp-Val-Tyr-NH₂

Z-Arg(Z,Z)-Pro-Asp(OBzl)-Val-Tyr-NH₂ (0.5 g) was hydrogenated with Pd-black (0.5 g) and ammonium formate (0.5 g) in CH₃OH (40 ml) overnight. The catalyst was filtered and the filtrate was removed on rotary evaporator. The residue was dissolved in H₂O and lyophilized. The crude peptide was then placed on a Sephadex DEAE column (60 cm×2.5 cm) and eluted with 0.01M NH₄HCO₃; pH 7.9. The flow rate was 90 ml/hr and fractions of 10 ml were collected. The peptide was eluted between tubes 17–29, which were pooled and lyophilized to give 290 mg of the title product.

Rf$_I$=0.32 (n-BuOH/HOAc/H₂O/Pyr=15:3:12:10; Silica Gel F60)

Rf$_{II}$=0.05 (n-BuOH/HOAc/H₂O=3:1:1; Silica Gel F60)

Amino Acid Analysis: Arg, 1.01; Pro, 1.01; Asp, 1.00; Val, 1.01; Tyr, 0.97 Peptide Content: 71 percent HPLC: Whatman Partisil—ODS column. 10 percent CH₃CN/0.02M KH₂PO₄ Buffer (pH 3.5). Flow rate: 3 ml/min.

The peptide has a retention time of 6.3 min and was 99.5 percent pure.

EXAMPLE XXII

Nα-Acetyl-Arginyl-2-Aminoisobutyryl-Aspartyl-Valyl-Tyrosine

The title compound was prepared by the solid phase method, starting with Boc(BrZ)Tyr benzyl ester resin (4.56 g. 0.44 meq/g). The following standard routines were used:

Deprotection—50 ml 50% TFA/CH₂Cl₂ for 5 min, then 50 ml 50% TFA/CH₂Cl₂ for 20 min;

Washing—50 ml CH₂Cl₂ twice for 1 min each, followed by 50 ml iPrOH for 1 min, then 50 ml CH₂Cl₂ twice for 1 min each;

Neutralization—50 ml 5% DIEA/CH₂Cl₂ twice for 2.5 min each;

Normal Coupling—6 mmol of the protected amino acid and HOBT (0.92 g) were dissolved in 4 ml DMF and then diluted with 41 ml CH₂Cl₂. DCC (1.24 g) was dissolved in 5 ml CH₂Cl₂, added to the mixture of reactants and resin and agitated for 2 h.

Symmetrical Anhydride Coupling—6 mmol of the protected amino acid was dissolved in 20:1 CH₂Cl₂:DMF (21 ml) and cooled to 0° C. DCC (0.83 g) was then added and the reaction mixture stirred for 30 min. After filtering, the filtrate was added to the resin and agitated for 20 h.

In sequence, the resin was coupled once each with Boc-Val, Boc(Bzl)$^\beta$-Asp, Boc-Aib, and Aoc$^\alpha$-Tos$^g$-Arg. The resin was recoupled once with Aoc$^\alpha$-Tos$^g$—Arg symmetric anhydride.

After deprotection, the resin peptide was acylated once with 10% Ac$_2$O in 1:1 DMF:CH$_2$Cl$_2$ (20 ml) and DMAP (300 mg) for 60 min. The resin was washed, air-dried and cleaved in HF/anisole (30 ml/8 ml) for 60 min at 0° C.

The resin residue was quenched in Et$_2$O and filtered. The solids were extracted with 1% NH$_4$OH (100 ml) for 1 h, filtered, and the extract lyophilized to give crude peptide as a colored solid, 600 mg.

The crude peptide was purified on DEAE Sephadex (2.6×86 cm column, 0.15M NH$_4$HCO$_3$, unbuffered; 100 ml/h flow rate, 12.5 ml/fraction, 277 nm detector). Fractions 109–119 were pooled and lyophilized to give the title compound, 230 mg.

| Amino Acid | Amino Acid Analysis: Ratio | |
|---|---|---|
| Arg | 0.98 | |
| Aib | 1.02 | |
| Asp | 1.00 | 64.4% peptide content |
| Val | 1.03 | |
| Tyr | 0.97 | |

| Thin Layer Chromatography 250 micron, Silica Gel G | | |
|---|---|---|
| | Elutent | R$_f$ |
| 4:1 | Trifluoroethanol:NH$_4$OH | 0.35 |
| 1:1:1:1 | n-BuOH:HOAc:H$_2$O:EtOAc | 0.62 |
| 15:3:12:10 | n-BuOH:HOAc:H$_2$O:Pyridine | 0.52 |

EXAMPLE XXIII

Arginyl-Cycloleucyl-Aspartyl-Valyl-Tyrosine

The title compound was prepared by the solid phase method, starting with Boc(Bzl)$^\beta$Asp-Val-Tyr(BrZ) benzylester resin (2.65 g, ca. 1.0 meq). The following standard routines were used:

Deprotection—40 ml 50% TFA/CH$_2$Cl$_2$ for 5 min, then 40 ml 50% TFA/CH$_2$Cl$_2$ for 20 min;

Washing—40 ml CH$_2$Cl$_2$ twice for 1 min each, followed by 40 ml iPrOH for 1 min, then 40 ml CH$_2$Cl$_2$ twice for 1 min each;

Neutralization—40 ml 5% DIEA/CH$_2$Cl$_2$ twice for 2.5 min each;

Coupling Procedure 1: 5.0 mmol of the protected amino acid and HOBT (0.77 g) were dissolved in 4 ml DMF and then diluted with 36 ml CH$_2$Cl$_2$. DCC (1.03 g) was dissolved in 5 ml CH$_2$Cl$_2$, added to the mixture of reactants and resin and agitated for 16 h.

Procedure 2: 8.0 mmol of the protected amino acid was dissolved in 40 ml CH$_2$Cl$_2$ and 1 ml DMF and cooled to 0° C. DCC (0.83 g) was then added and the reaction stirred for 30 min. The solids were filtered, the filtrate added to the resin and agitated for 3 h.

Procedure 3: 5.0 mmol of the protected amino acid active ester and HOBT (0.77 g) were dissolved in 20 ml DMF and 20 ml CH$_2$Cl$_2$. This solution was added to the resin and agitated for 24 h.

Procedure 4: 5.0 mmol of the protected amino acid active ester and DMAP (0.5 g) were dissolved in 20 ml DMF and 20 ml CH$_2$Cl$_2$. This solution was added to the resin and agitated 68 h.

In sequence, the resin was coupled once with Boc-Cle via procedure, 1, Z$_3$-Arg-ONp via procedure 3, recoupling once with Aoc$^\alpha$-Tos$^g$-Arg via procedure 2, and finally with Z$_3$-Arg-ONp via procedure 4. After deprotection, the resin was washed, air-dried and cleaved in HF/anisole (30 ml/8 ml) for 60 min at 0° C.

The resin residue was quenched in Et$_2$O and filtered. The solids were extracted with 1% NH$_4$OH (100 ml) for 1 h, filtered, adjusted to pH 6 with HOAc and the extract lyophilized to give crude peptide as a colorless solid, 720 mg.

The crude peptide was purified on DEAE Sephadex (2.6×85 cm column, 0.12M NH$_4$HCO$_3$, unbuffered; 100 ml/h flow rate, 12.5 ml/fraction, 206 nm detector). Fractions 317–370 were pooled and lyophilized to give the desired material. The peptide was desalted on G-10 Sephadex (2.6×83 cm, column, 1% HOAc as elutent, 3 ml/h flow rate, 4 ml/fraction, 277 nm detector). Fraction 78–105 were pooled and lyophilized to give the title compound, 395 mg.

| Amino Acid | Amino Acid Analysis: Ratio | |
|---|---|---|
| Arg | 1.00 | |
| Cle | 1.05 | |
| Asp | 0.98 | 75.8% peptide content |
| Val | 1.00 | |
| Tyr | 0.98 | |

| Thin Layer Chromatography 250µ micron, Silica Gel G | | |
|---|---|---|
| | Elutent | R$_f$ |
| 15:3:12:10 | n-BuOH:HOAc:H$_2$O:Pyridine | 0.55 |
| 1:1:1:1 | n-BuOH:HOAc:H$_2$O:EtOAc | 0.60 |
| 4:1: | Trifluoroethanol:NH$_4$OH | 0.21 |

EXAMPLE XXIV

N$^\alpha$-Acetyl-Arginyl-Prolyl-Aspartyl-Valyl-Tyrosyl-Glycine amide

The title compound was prepared by the solid phase method, starting with p-methylbenzhydrylamine resin (U.S. Biochemical 31578, 4.2 g, 0.25 meq/g). The following standard routines were used:

Deprotection—40 ml 50% TFA/CH$_2$Cl$_2$ for 1 min, then 50 ml 40% TFA/CH$_2$Cl$_2$ for 30 min;

Washing—40 ml CH$_2$Cl$_2$ twice for 1 min each, followed by 40 ml iPrOH for 1 min, then 40 ml CH$_2$Cl$_2$ twice for 1 min each;

Neutralization—40 ml 5% DIEA/CH$_2$Cl$_2$ twice for 2.5 min each;

Coupling—3.0 mmol of the protected amino acid and HOBT (0.46 g) were dissolved in 2 ml DMF and then diluted with 28 ml CH$_2$Cl$_2$. DCC (0.62 g) was dissolved in 5 ml CH$_2$Cl$_2$, added to the mixture of reactants and resin and agitated for 2 h.

In sequence, the resin was coupled once with BOC-Gly, BOC-Tyr(BrZ), BOC-Val, BOC-Bzl$^\beta$-Asp, BOC-Pro, and AOC$^\alpha$-Tos$^g$-Arg. After deprotection, the resin peptide was acylated once with 10 percent Ac$_2$O in 1:1 DMF:CH$_2$Cl$_2$ (18 ml) and DMAP (0.3 g) for 60 min. The resin was washed, air-dried and cleaved in HF/anisole (30 ml/8 ml) for 1 h at 0° C.

The resin residue was quenched in Et$_2$O and filtered. The solids were extracted with 0.3% NH$_4$OH (100 ml) for 1 h, filtered, and the extract lyophilized to give crude peptide as a colorless solid, 720 mg.

The crude peptide was purified on DEAE Sephadex (2.6×89 cm column, 0.03M NH$_4$HCO$_3$, unbuffered; 75 ml/h, 7 ml/fraction, 278 nm detector). Fractions 42—52 were pooled and lyophilized to give the title compound, 425 mg.

| Amino Acid Analysis | | |
|---|---|---|
| Amino Acid | Ratio | |
| Arg | 1.03 | |
| Pro | 1.01 | |
| Asp | 0.99 | 79.5% peptide content |
| Val | 0.99 | |
| Tyr | 1.01 | |
| Gly | 0.97 | |

| Thin Layer Chromatography 250 Silica Gel G | | |
|---|---|---|
| | Elutent | R$_f$ |
| 3:1:1 | n-BuOH:HOAc:H$_2$O | 0.23 |
| 1:1:1:1 | n-BuOH:HOAc:H$_2$O:EtOAc | 0.59 |
| 4:2:3:1 | n-BuOH:HOAc:H$_2$O:Pyridine | 0.71 |

EXAMPLE XXV

Following peptide preparation methods similar to those employed in Examples I–XXIV, there were prepared the following:

A. N-α-Acetyl-Arginyl-Prolyl-Aspartyl-Valyl-N-α-methyl-Tyrosine, solvated

Amino acid analysis: Arg-1.02; Pro-1.00; Asp-1.00; Val-1.04; 73.5% peptide content Thin Layer Chromatography Silica Gel G 250F hard surface

| | Eluent | R$_f$ |
|---|---|---|
| 3:1:1 | n-BuOH:HOAc:H$_2$O | 0.50 |
| 4:2:3:1 | n-BuOH:HOAc:H$_2$O:Pyridine | 0.74 |
| 2:2:1 | CHCl$_3$:MeOH: conc. NH$_4$OH | 0.76 |

B. Arginyl-4-methyl-leucyl-Aspartyl-Valyl-Tyrosine, Solvated

Amino Acid Analysis: Asp-1.00; Val-1.00; Tyr-0.96; Arg-100; 4-Me-Leu-0.96; 93.0% peptide content

| Thin Layer Chromatography Silica Gel 60 | | |
|---|---|---|
| | Eluent | R$_f$ |
| 1:1:1:1 | n-BuOH:HOAc:H$_2$O:EtOAc | 0.60 |
| 15:3:12:10 | n-BuOH:HOAc:H$_2$O:Pyridine | 0.48 |
| 4:2:3:1 | n-BuOH:HOAc:H$_2$O:Pyridine | 0.61 |

EXAMPLE XXVI

Induction Assay

Prothymocytes (Thy-1$^-$) and pro-Lyb-2 cells were coenriched from B6-lyb-2.1 congenic mouse spleen by BSA density gradient centrifugation (Pathocyte 5, Miles Laboratories, lot 35, 1 ml of 35:29:26:23:18:12%). The 26:23 and 23:28 interface layers were combined, and Thy-1+ and Lyb-2+ cells removed by reaction with monoclonal Thy-1.2 and Lyb-2.1 antibodies and adherence to plates coated with affinity-purified rabbit anti mouse F(ab)$_2$. The washed non-adherent cells were used for both assays. This starting population contains 30–40% prothymocytes and 30–40% pro-Lyb-2 cells (known to represent separate committed precursor populations). Five ×10$^6$ cells/0.5 ml RPMI 1640 were incubated in 5 ml plastic tubes with equal volumes of inducer in serial dilution in RPMI 1640 in a humidified 5% CO$_2$ atmosphere for 3 hrs. The cells were then assayed separately for Thy-1 and Lyb-2.1 expression with monoclonal antibodies in optimal concentration by the Protein-A-SRBC method of Scheid and Triglia, Immunogenet., 9, 423–433 (1979) (controls without inducer register <5% induced cells). The subject peptides stimulate induction of Thy-1+ cells (T cells) and thus are designated as possessing biological activity. The subject peptides wherein X is GLU or D-GLU also stimulate induction of Lyb-2.1+ cells (B cells), as well as T cells. For comparison, a control peptide NH$_2$-TYR-ARG-LYS-ASP-VAL-OH stimulated no induction of either T cells or B cells.

EXAMPLE XXVII

Receptor Assay

Materials—CEM cell lines were obtained from the American Type Culture Collection. 3-Nitro-2-pyridine sulfonyl chloride and 2-pyridinethiol 1-oxide were provided by Dr. Rei Matsueda, Sanyo Laboratories, Tokyo. RPMl-1640, fetal bovine serum and L-glutamine were obtained from Gibco, gentamycin from Schering, and lectin-coupled agarose beads from Vector Laboratories. Sephadex was purchased from Pharmacia Fine Chemicals, rabbit antithymopoietin antibody from Accurate Chemical Scientific Corp., ubiquitin from Peninsula Laboratory, and human IgG from Miles Laboratories. All other chemicals were purchased from common commercial sources and were of reagent grade.

The abbreviations used are: PBS, phosphate-buffered saline; TCA, trichloroacetic acid; SDS, sodium dodecylsulfate; Con A, concanavilin A; TP, thymopoietin; PEG, polyethylene glycol; BSA, bovine serum albumin; I.P., intraperitoneal; PMSF, phenyl methyl sulfonyl fluoride; FTS, facteur thymique serique; CRF, corticotropin-releasing factor; ACTH, adrenocorticotropic hormone; Hepes, N-2-hydroxyethylpiperazine N-2-ethane-sulfonic acid.

Cyclic Nucleotide Assays—The CEM cell line was grown for different periods of time and was harvested as described below. The cells were washed three times in PBS, resuspended in RPMI-1640 at a concentration of 3.12×10$^7$ cells/ml and allowed to equilibrate at 37° C. for 30 min before the addition of 100 ng bovine thymopoietin (25 μl; 4.0 μg/ml) to 1 ml of cells. The incubation was continued for 4–5 min in a shaking water bath and was then terminated by the addition of 1 ml ice-cold 10 percent TCA with homogenization and sonication to release the cyclic nucleotides. The suspension was centrifuged at 3000×g for 20 min at 4° C. The precipitate was dissolved in 0.1N NaOH, and the protein content determined by the method of Cadman, et al., Anal Biochem, 96,21–23. TCA was removed from the supernatant by extracting four times with 5 ml of water saturated diethyl ether. After the final extraction, the remaining traces of ether were removed by heating for 10 min in a 50° C. water bath. The sample was lyophilized and reconstituted in 50 mM acetate buffer, pH 6.2, for radioimmunoassay of cyclic nucleotides.

Preparation of Membrane Glycoprotein—The CEM human lymphoid cell line was cultured in RPMI-1640 supplemented with 10 percent heat-inactivated fetal bovine serum, 2 mM fetal bovine serum, 2 mM L-glutamine and 50 μg/ml gentamycin at 37° C. in a humid atmosphere containing 5 percent CO$_2$, to a final density of 3–4×10$^6$ cells/ml. At this concentration, cells were in the early stationary phase of the growth curve and were judged greater than 90 percent viable by trypan blue exclusion.

Membrane glycoproteins were prepared by a modification of the technique of Hedo, et al., Biochem, 20, 3385–3393. The cells were washed once with PBS and were suspended in 40 percent sucrose, 50 50 mM Hepes, 1 percent EDTA, 0.1 percent O-phenanthroline, and 1 mM PMSF (in methanol), pH 7.8, and homogenized in a glass homogenizer at room temperature. The total suspension was then subjected to sonication by a cell disruptor sonicator with a cup horn attachment (Model W-225R) at 35° C. for 10 min. The suspension was centrifuged at 600×g for 10 min at 4° C. in a Sorval GLC-3 centrifuge, and the supernatant was recentrifuged at 20,000×g in a Sorval 5B centrifuge at 4° C. for 3 min. The crude membrane fraction obtained from this pellet was suspended in 50 mM Hepes, 10 mM $MgSO_4$, and 1 mM PMSF, pH 7.8, at a final protein concentration of 5 mg/ml. Solubilization of protein was performed by stirring the suspension for 2 h at 25° C. in the presence of 1 percent Triton X-100 (final concentration) and 0.1 percent brij-96 (polyoxyethylene 10, oleyl ether) (final concentration). The suspension was centrifuged at 2,000×g for 2 h at 4° C., and the supernatant was stored at −70° C. Soluble protein concentration was measured according to the technique of Cadman, et al., using BSA as a standard and buffer as a control.

Wheat germ agglutinin or ricinus communis agglutinin-I was used for purification of the receptor protein. All lectin beads were stored at 4° C. with their corresponding monosaccharide inhibitors (300 mM).

For each purification 2 ml of lectin-agarose was packed into a 1 cm diameter column and washed at room temperature with 25 ml of 0.15M NaCl, 50 mM Hepes, 0.1 percent Triton X-1 and 0.01 percent SDS, pH 7.8.

The columns were washed with 200 ml of 0.15M NaCl, 50 mM Hepes and 0.1 percent Triton X-100, pH 7.8, followed by a final wash of this buffer containing 10 mM $MgSO_4$. PMSF (1 mM) was added to all the buffer systems. Solubilized membrane proteins (∼10 mg) were recycled five times through individual columns. The column was then washed with 100 ml of 0.15M NaCl, 50 mM Hepes, 10 mM MgSO and 0.1 percent Triton X-100, pH 7.8, at 4° C. Monosaccharide inhibitors, at a concentration of 400 mM in 3 ml washing buffer, were used for individual column elutions; N-acetyl glucosamine for wheat germ agglutinin and β-methyl D-galactoside for ricinus communis agglutinin-I. The monosaccharides were applied to the column, which was stopped for 30–40 min to permit equilibration and then eluted further. The protein eluate was dialyzed against 500 ml of 50 mM Hepes, 10 mM $MgSO_4$ and 0.1 percent Triton X-100, pH 7.8, at 4° C.

Preparation of Radiolabelled Thymopoietin— Thymopoietin was dissolved in 2.0M sodium carbonate-bicarbonate buffer, pH 9.8, to obtain free amino groups. 3-nitro-2-pyridine sulfonyl chloride in dioxane (10:1 moles) was added to the thymopoietin solution and stirred for 5 h at 20° C. After the addition of water the insoluble material was centrifuged. The protected peptide was purified using Sephadex G-25 chromatography followed by digestion with post-proline cleaving enzyme to remove the $NH_2$-terminal blocked proline. Methyl 3,5 di[$^{125}$I]iodohydroxybenzimidate (4000 Ci/mM) was obtained at a concentration of 5.5 mCi/ml in methanol and was evaporated to dryness. The iodinated imidoester (1.4 nM) was reacted with protected thymopoietin (5 μg; 0.9 nM) according to the method of Wood, et al., Anal. Biochem., 69, 339–349, with the following modifications. The reaction was carried out in 500 μl of 0.16M borate buffer, pH 9.1, for 24 h at 4° C. The reaction was stopped by the addition of 500 μl of 2M citrate phoshate buffer, pH 5.5, at 4° C. The sample was chromatographed on a Biogel P-10 column in sodium pyrophosphate, pH 7.5 (15 drops/fraction), at 4° C. to separate the free iodine.

The iodinated peptide was dissolved in water and treated with 2-pyridinethiol 1-oxide (10:1 moles) for 5 h at room temperature to remove the protecting groups. The labelled peptide was purified on a Biogel P-10 column. Three radioactive peaks were obtained, the first two of which were immunoactive with rabbit anti-thymopoietin antibody. The first peak was then applied to a 1×60 cm column of DEAE-Sephadex A-25 that had been equilibrated with 50 mM Tris buffer, pH 7.0. The iodination mixture was eluted with this buffer using a linear gradient of increasing ionic strength from the equilibration concentration up to 1.0M. The radioactivity of each fraction was determined using an LKB 1280 Ultra gamma spectrometer.

Fractions with peak radioactivity from each purification scheme were analyzed for binding with excess antithymopoietin antibody. Fractions from peak II (fractions 35–45) of the DEAE-Sephedex A-25 column showed the highest specific binding and were used subsequently in the radioreceptor assay.

Iodinated thymopoietin retained biological activity as determined by assessing its effect in a neuromuscular assay (Goldstein, Nature, 247, 11–14 (1974)) and its effect on the synthesis of cyclic GMP by CEM cells.

Binding Assay—The assay buffer was prepared by adding 12 g Hepes, 1.2 g $MgSO_4$ and 1.2 g BSA to 1000 ml of glass distilled water. A pH of 7.65 was obtained using 1N NaOH. The stock standard solution was made using assay buffer and was used for one week. The assay was performed in 12×75 mm glass test tubes by the addition of 100 μl of standard solution, 25 μl of receptor protein (150-200 μg/ml), 25 μl $^{125}$I-TP (80,000 cpm) 20 μl of 1 percent Triton X-100, and the volume was made up to 200 μl with assay buffer. After incubation for 18 h at 4° C., 200 μl of human IgG (1.5 mg/ml) (as carrier) and 200 μl of 35 percent PEG-8000 in PBS, pH 7.56, were added, mixed, and incubated for 30 min on ice. The tubes were centrifuged and the residue was washed with 10 percent PEG in PBS, pH 7.3, and counted in an LKB-gamma counter.

The radioactivity in the precipitate in the presence of 1 mg/ml nonradioactive thymopoietin was taken to represent nonspecific binding. TCA was added to the supernatant (final concentration 5 percent) and precipitable radioactivity was measured. At all times this exceeded 95 percent, indicating minimal release of free $^{125}$I from the tracer.

Competition Experiments—Following the above binding assay procedure, 2.3×10$^{-10}$M of $^{125}$I-TP was incubated with 4 g of binding protein and test peptide. The incubation was continued for 12 h and free and bound $^{125}$I-TP was determined as above. The following representative compounds of the invention caused displacement at least least 50% of that caused by thymopoietin self-displacement at equivalent concentrations:

N-α-acetyl-ARG-PRO-ASP-GLN-TYR-OH;
N-α-acetyl-ARG-PRO-ASP-ALA-TYR-OH;
N-α-acetyl-ARG-PRO-ASP-GLU-TYR-OH;
N-α-acetyl-ARG-PRO-ASP-ILE-TYR-OH;

N-α-acetyl-ARG-PRO-ASP-LYS-TYR-OH;
N-α-acetyl-ARG-PRO-ASP-VAL-TYR-NH₂;
H₂N-ARG-AIB-ASP-VAL-TYR-OH;
N-α-acetyl-ARG-PRO-ASP-VAL-TYR-NHCH₃;
H-ARG-PRO-ASP-VAL-TYR-NH₂;
N-α-acetyl-ARG-PRO-ASP-VAL-TYR-OH; and
N-α-formyl-ARG-PRO-ASP-VAL-TYR-OH.

For comparison, other peptides such as insulin, glucagon, growth hormone, somatostatin, β-endorphin, FTS, ACTH, CRF, and ubiquitin caused no detectable displacement.

The above Examples have been provided to illustrate the subject invention but not to limit its scope, which scope is set out only in the appended claims.

What is claimed is:

1. A peptide having the formula:

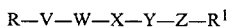

or a pharmaceutically acceptable acid- or base-addition salt thereof, wherein:
R is H, NH₂, acyl-NH, CH₃NH, or pyro-GLU-NH;

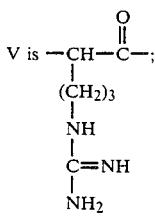

W is PRO, dehydro PRO, or

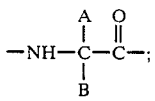

A individually is C₂-C₆ loweralkyl;
B individually is C₁-C₃ loweralkyl;
A and B taken together are —(CH₂)₄— or —(CH₂)₅—;
X is D-ASP, ASP, D-GLU, or GLU;
Y is GLY, VAL, LEU, nor-LEU, PHE, ILE, LYS, GLN, GLU, ALA, D-VAL, D-LEU, D-nor LEU, D-PHE, D-ILE, D-LYS, D-GLN, D-GLU, or D-ALA;
Z is

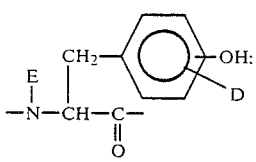

D is H or 1 or 2 substituents which increase or do not substantially decrease the acidity of the phenol proton;
E is H or C₁-C₃ loweralkyl;
R¹ is OH, NHR″,

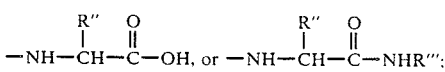

and
R″ and R‴ are individually H or lower alkyl;
provided that V may be D- or L-isomer if R is other than H, and further provided that no more than one of V, X, and Y is a D amino acid.

2. A peptide having the formula:

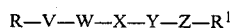

or a pharmaceutically acceptable acid- or base-addition salt thereof, wherein:
R—V is acyl-ARG or acyl-D-ARG;
W is PRO or AIB
X is D-ASP, ASP, D-GLU, or GLU;
Y is GLY, VAL, LEU, norLEU, PHE, ILE, LYS, GLN, GLU, ALA, D-VAL, D-LEU, D-norLEU, D-PHE, D-ILE, D-LYS, D-GLN, D-GLU, or D-ALA;
Z is

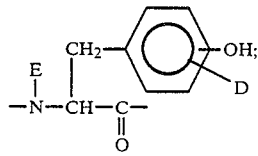

D is H or 1 or 2 substituents which increase or do not substantially decrease the acidity of the phenol proton;
E is H or C₁-C₃ loweralkyl;
R¹ is OH, NHR″,

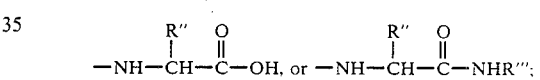

and
R″ and R‴ are individually H or lower alkyl;
provided that no more than one of V, X, and Y is a D amino acid.

3. A peptide having the formula:

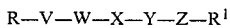

or a pharmaceutically acceptable acid- or base-addition salt thereof, wherein:
R—V is acyl-ARG;
W is PRO or AIB;
X is ASP or GLU;
Y is GLY, VAL, LEU, norLEU, PHE, ILE, LYS, GLN, GLU, or ALA;
Z is

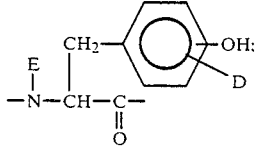

D is H or 1 or 2 substituents which increase the acidity of the phenol proton;
E is H or C₁-C₃ loweralkyl;
R¹ is OH or NH₂.

4. The peptide of claim 3 wherein R—V is acetyl-ARG and R¹ is NH₂.

5. The peptide of claim 3 which is N-α-acetyl-ARG-PRO-ASP-VAL-TYR-NH₂.

6. The peptide of claim 3 which is N-α-acetyl-ARG-PRO-ASP-GLU-TYR-OH.

7. The peptide of claim 3 which is N-α-succinoyl-ARG-PRO-ASP-VAL-TYR-OH.

8. The peptide of claim 3 which is N-α-formyl-ARG-PRO-ASP-VAL-TYR-OH.

9. The peptide of claim 3 which is N-α-acetyl-ARG-PRO-ASP-ILE-TYR-OH.

10. The peptide of claim 2 which is N-α-acetyl-D-ARG-PRO-ASP-VAL-TYR-OH.

11. The peptide of claim 3 which is N-α-acetyl-ARG-PRO-ASP-PHE-TYR-OH.

12. The peptide of claim 3 which is N-α-acetyl-ARG-PRO-ASP-GLN-TYR-OH.

13. The peptide of claim 2 which is N-α-acetyl-ARG-PRO-ASP-VAL-D-TYR-OH.

14. The peptide of claim 3 which is N-α-acetyl-ARG-PRO-ASP- VAL-TYR-OH.

15. The peptide of claim 1 which is NH₂-ARG-D-PRO-ASP-VAL-TYR-OH.

16. The peptide of claim 2 which is

N—α-acetyl-ARG—PRO—
—ASP—VAL—TYR—NH—CH₂—CH—CH₃.
                              |
                              CH₃

17. The peptide of claim 3 which is N-α-acetyl-ARG-PRO-ASP-ALA-TYR-OH.

18. The peptide of claim 2 which is N-α-acetyl-ARG-PRO-ASP-VAL-TYR-NH-CH₃.

19. The peptide of claim 3 which is N-α-acetyl-ARG-PRO-GLU-VAL-TYR-NH₂.

20. The peptide of claim 2 which is N-α-acetyl-D-ARG-PRO-ASP-VAL-TYR-NH₂.

21. The peptide of claim 2 which is N-α-acetyl-ARG-AIB-ASP-VAL-TYR-NH₂.

22. The peptide of claim 1 which is N-α-acetyl-ARG-3,4-dehydro-PRO-ASP-VAL-TYR-NH₂.

23. The peptide of claim 1 which is NH₂-ARG-PRO-ASP-VAL-TYR-NH₂.

24. The peptide of claim 3 which is N-α-acetyl-ARG-AIB-ASP-VAL-TYR-OH.

25. The peptide of claim 1 which is NH₂-ARG-CLE-ASP-VAL-TYR-OH.

26. The peptide of claim 1 which is N-α-acetyl-ARG-PRO-ASP-VAL-TYR-GLY-NH₂.

27. The peptide of claim 3 which is N-α-acetyl-ARG-PRO-ASP-VAL-N-α-methyl-TYR-OH.

28. The peptide of claim 1 which is NH₂-ARG-4-methyl-LEU-ASP-VAL-TYR-OH.

* * * * *